US009542771B2

United States Patent
Noshi et al.

(10) Patent No.: US 9,542,771 B2
(45) Date of Patent: Jan. 10, 2017

(54) IMAGE PROCESSING SYSTEM, IMAGE PROCESSING APPARATUS, AND IMAGE PROCESSING METHOD

(71) Applicant: Toshiba Medical Systems Corporation, Otawara-shi (JP)

(72) Inventors: Yasuhiro Noshi, Otawara (JP); Tatsuo Maeda, Nasushiobara (JP); Akira Adachi, Otawara (JP); Takumi Hara, Akishima (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 252 days.

(21) Appl. No.: 14/081,312

(22) Filed: Nov. 15, 2013

(65) Prior Publication Data

US 2014/0071132 A1   Mar. 13, 2014

Related U.S. Application Data

(63) Continuation of application No. PCT/JP2012/061889, filed on May 9, 2012.

(30) Foreign Application Priority Data

May 16, 2011   (JP) ................................. 2011-109683

(51) Int. Cl.
*G06T 15/08*   (2011.01)
*A61B 6/00*   (2006.01)
(Continued)

(52) U.S. Cl.
CPC .............. *G06T 15/08* (2013.01); *A61B 6/022* (2013.01); *A61B 6/466* (2013.01); *A61B 6/5211* (2013.01);
(Continued)

(58) Field of Classification Search
CPC ......... G06T 15/08; A61B 6/022; A61B 6/466; A61B 6/5211; A61B 8/466; A61B 8/5215; H04N 13/0055; H04N 13/0242; H04N 13/0275; H04N 13/0282
See application file for complete search history.

(56) References Cited

U.S. PATENT DOCUMENTS

| | | | | |
|---|---|---|---|---|
| 5,162,779 A | * | 11/1992 | Lumelsky | G06F 3/04812 345/157 |
| 5,712,965 A | * | 1/1998 | Fujita | G06T 19/20 345/419 |

(Continued)

FOREIGN PATENT DOCUMENTS

| | | |
|---|---|---|
| CN | 101241604 A | 8/2008 |
| CN | 101587386 A | 11/2009 |

(Continued)

OTHER PUBLICATIONS

Barham et al. "Comparison of Stereoscopic Cursors for the Interactive Manipulation of B-Splines." Electronic Imaging '91, San Jose, CA. International Society for Optics and Photonics, 1991.*

(Continued)

*Primary Examiner* — Ke Xiao
*Assistant Examiner* — Jed-Justin Imperial
(74) *Attorney, Agent, or Firm* — Oblon, McClelland, Maier & Neustadt, L.L.P.

(57) ABSTRACT

An image processing system according to an embodiment includes a stereoscopic display apparatus, a rendering processor, and a display controller. The stereoscopic display apparatus displays a stereoscopic image enabled for a stereoscopic vision using a plurality of parallax images. The rendering processor generates a plurality of parallax images by applying a rendering process to volume data that is three-dimensional medical image data from a plurality of viewpoint positions having different relative positions with (Continued)

respect to the volume data. The display controller causes the stereoscopic display apparatus to display a graphic image that is an image of a given graphic indicating a depth-direction position of a cursor that is operable by a given input unit in a three-dimensional stereoscopic image space in which a stereoscopic image is displayed, together with the parallax images.

17 Claims, 15 Drawing Sheets

(51) Int. Cl.
*A61B 6/02* (2006.01)
*A61B 8/00* (2006.01)
*A61B 8/08* (2006.01)
*H04N 13/00* (2006.01)
*H04N 13/02* (2006.01)

(52) U.S. Cl.
CPC ............... *A61B 8/466* (2013.01); *A61B 8/483* (2013.01); *A61B 8/5215* (2013.01); *H04N 13/0275* (2013.01); *H04N 13/0282* (2013.01)

(56) References Cited

U.S. PATENT DOCUMENTS

| | | | | |
|---|---|---|---|---|
| 5,774,111 | A * | 6/1998 | Lecland | G06F 3/04845 345/666 |
| 6,088,019 | A * | 7/2000 | Rosenberg | A63F 13/06 345/156 |
| 7,307,631 | B2 * | 12/2007 | Robart | G06T 15/60 345/422 |
| 7,509,592 | B1 * | 3/2009 | Martinez | G06F 3/04812 715/862 |
| 7,834,903 | B2 | 11/2010 | Saishu et al. | |
| 8,125,513 | B2 | 2/2012 | Saishu et al. | |
| 8,823,706 | B2 * | 9/2014 | Helbling | G06F 17/50 345/418 |
| 2002/0032696 | A1 * | 3/2002 | Takiguchi | G06F 17/30126 715/255 |
| 2011/0122234 | A1 * | 5/2011 | Kikkawa | G06T 7/0022 348/51 |
| 2011/0235066 | A1 * | 9/2011 | Sakuragi | G06T 7/0022 358/1.6 |

FOREIGN PATENT DOCUMENTS

| | | |
|---|---|---|
| JP | 60-222919 | 11/1985 |
| JP | 62-137673 | 6/1987 |
| JP | 02-150968 | 6/1990 |
| JP | 04-037405 | 3/1992 |
| JP | 2005-086414 | 3/2005 |

OTHER PUBLICATIONS

Combined Office Action and Search Report issued on Aug. 6, 2015 in Chinese Patent Application No. 201280000967.9 with English translation.

International Search Report issued on Jun. 26, 2012 for PCT/JP2012/061889 filed on May 9, 2012 with English Translation.

International Written Opinion issued on Jun. 26, 2012 for PCT/JP2012/061889 filed on May 9, 2012.

Chinese Office Action issued Oct. 8, 2014, in Chinese Office Action 201280000967.9.

* cited by examiner

WORKSTATION 130

TERMINAL APPARATUS 140

FIG.13
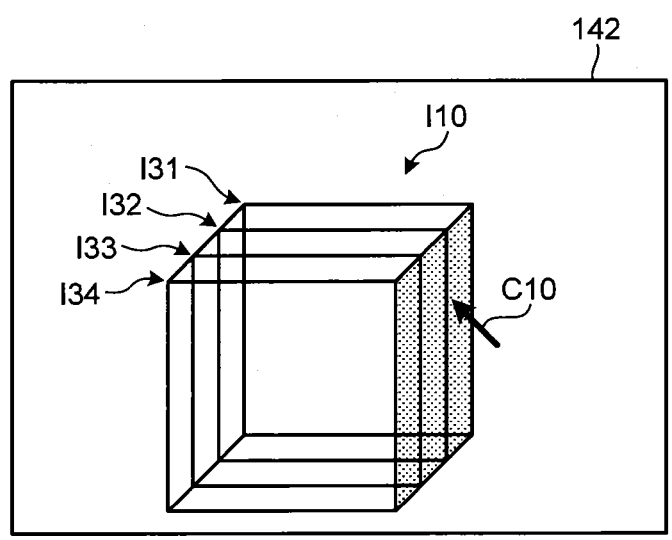
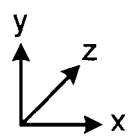

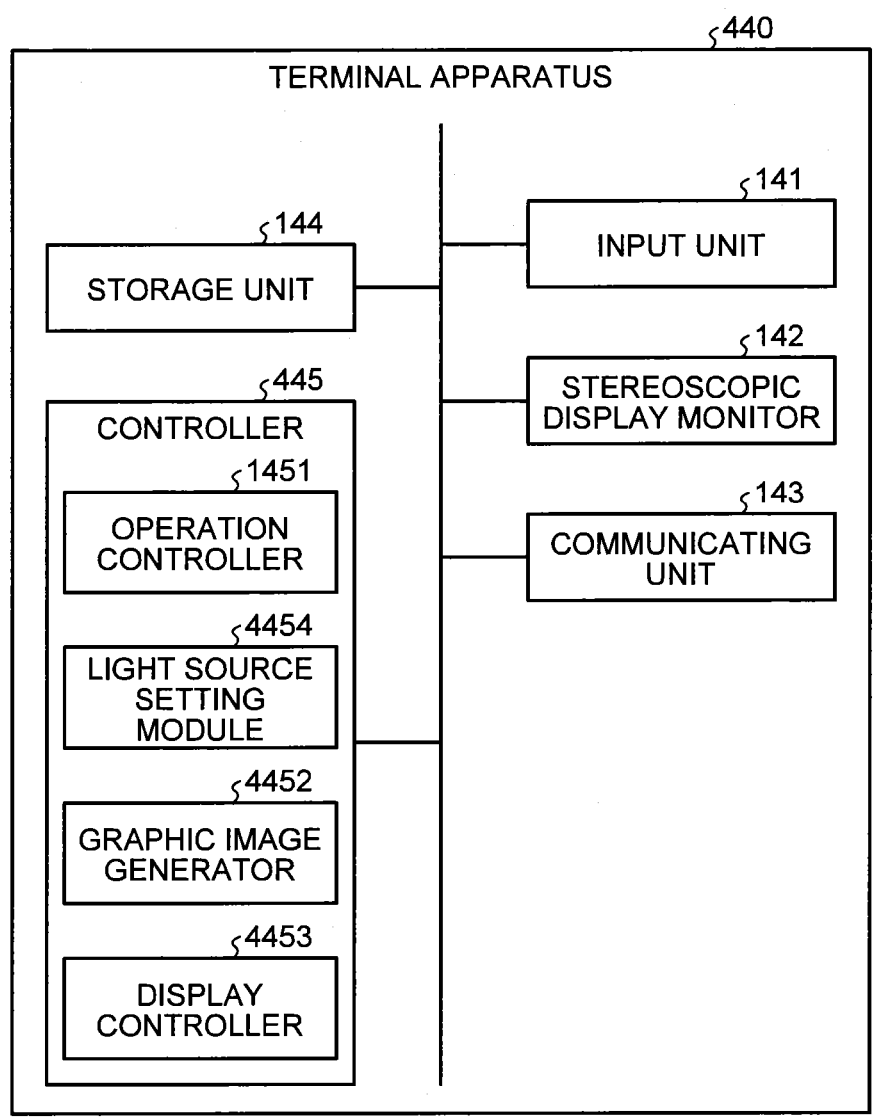

FIG.18
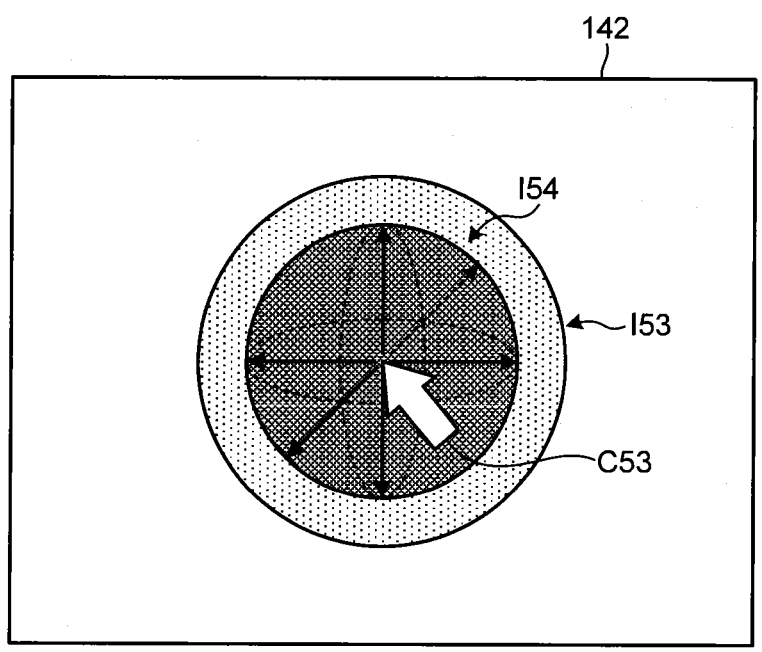
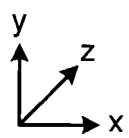

IMAGE PROCESSING SYSTEM, IMAGE PROCESSING APPARATUS, AND IMAGE PROCESSING METHOD

CROSS-REFERENCE TO RELATED APPLICATIONS

This application is a continuation of International Application No. PCT/JP2012/061889, filed on May 9, 2012 which claims the benefit of priority of the prior Japanese Patent Application No. 2011-109683, filed on May 16, 2011, the entire contents of which are incorporated herein by reference.

FIELD

Embodiments described herein relate generally to an image processing system, an image processing apparatus, and an image processing method.

BACKGROUND

Conventionally available is a technology that displays a stereoscopic image to a user using special equipment such as a pair of stereoscopic glasses, by displaying two parallax images captured from two viewpoints on a monitor. In addition, recently available is a technology for displaying a stereoscopic image to a user with naked eyes, by displaying multiple-parallax images (e.g., nine parallax images) captured from a plurality of viewpoints on a monitor, using a light ray controller such as a lenticular lens.

At the same time, some medical image diagnostic apparatuses such as X-ray computed tomography (CT) apparatuses, magnetic resonance imaging (MRI) apparatuses, and ultrasonic diagnostic apparatuses are capable of generating three-dimensional medical image data (hereinafter, volume data). Such a medical image diagnostic apparatus also generates a two-dimensional image to be displayed by applying various imaging processes to the volume data, and displays the two-dimensional image on a general-purpose monitor. For example, such a medical image diagnostic apparatus generates a two-dimensional image of a cross-sectional surface of a subject reflected with the three-dimensional information by executing a volume rendering process to the volume data, and displays the two-dimensional image thus generated on a general-purpose monitor.

BRIEF DESCRIPTION OF THE DRAWINGS

FIG. 13 is a schematic illustrating an example of a stereoscopic image displayed on a stereoscopic display monitor in a second embodiment;

FIG. 15 is a schematic for explaining an exemplary configuration of a terminal apparatus in a fourth embodiment;

FIG. 18 is a schematic for explaining an example for displaying a stereoscopic image in which contrast is increased only in a given area.

DETAILED DESCRIPTION

An image processing system according to an embodiment includes a stereoscopic display apparatus, a rendering processor, and a display controller. The stereoscopic display apparatus displays a stereoscopic image enabled for a stereoscopic vision using a plurality of parallax images. The rendering processor generates a plurality of parallax images by applying a rendering process to volume data that is three-dimensional medical image data from a plurality of viewpoint positions having different relative positions with respect to the volume data. The display controller causes the stereoscopic display apparatus to display a graphic image that is an image of a given graphic indicating a depth-direction position of a cursor that is operable by a given input unit in a three-dimensional stereoscopic image space in which a stereoscopic image is displayed, together with the parallax images.

Hereinafter, embodiments of an image processing system, an image processing apparatus, and an image processing method are explained in detail with reference to the accompanying drawings. To begin with, terms used in the embodiment below will be explained. A "parallax image group" is a group of images generated by applying a volume rendering process to volume data while shifting viewpoint positions by a given parallax angle. In other words, a "parallax image"

group" includes a plurality of "parallax images" each of which has a different "viewpoint position". A "parallax angle" is an angle determined by adjacent viewpoint positions among viewpoint positions specified for generation of the "parallax image group" and a given position in a space represented by the volume data (e.g., the center of the space). A "parallax number" is the number of "parallax images" required for providing a stereoscopic vision on a stereoscopic display monitor. A "nine-parallax image" mentioned below means a "parallax image group" with nine "parallax images". A "two-parallax image" mentioned below means a "parallax image group" with two "parallax images".

First Embodiment

Figure 1:
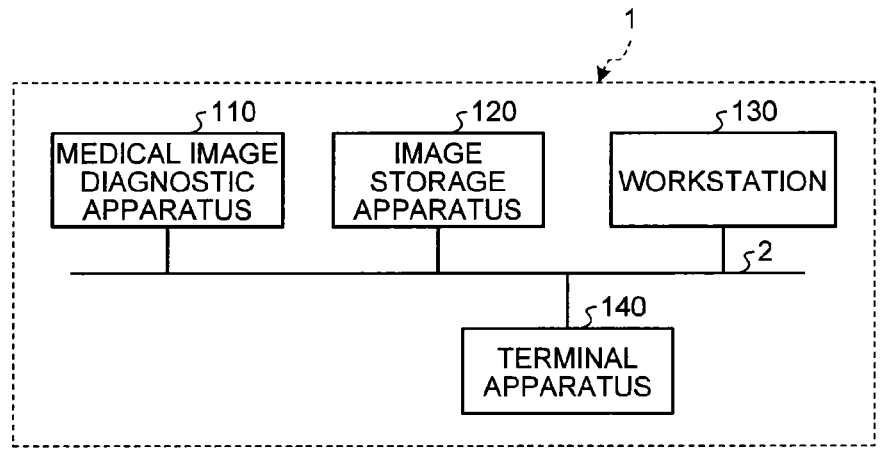
FIG. 1 is a schematic for explaining an exemplary configuration of an image processing system according to a first embodiment.

An exemplary configuration of an image processing system according to a first embodiment will now be explained. FIG. 1 is a schematic of an exemplary configuration of the image processing system according to the first embodiment.

As illustrated in FIG. 1, an image processing system 1 according to the first embodiment includes a medical image diagnostic apparatus 110, an image storage apparatus 120, a workstation 130, and a terminal apparatus 140. The apparatuses whose examples are illustrated in FIG. 1 are communicative with each other directly or indirectly over an internal local area network (LAN) 2 deployed in a hospital and the like. When a picture archiving and communication system (PACS) is installed on the image processing system 1, for example, each of the apparatuses exchanges medical images and the like with the others based on the Digital Imaging and Communications in Medicine (DICOM) standard.

Such an image processing system 1 generates a parallax image group from volume data that is three-dimensional medical image data generated by the medical image diagnostic apparatus 110, and displays the parallax image group on a monitor capable of providing a stereoscopic vision. In this manner, the image processing system 1 provides an observer, such as a physician or an examiner who is working in the hospital, with a stereoscopic image that is an image that can be stereoscopically perceived by the observer. Specifically, in the first embodiment, the workstation 130 applies various image processes to the volume data, to generate a parallax image group. The workstation 130 and the terminal apparatus 140 have a monitor capable of providing a stereoscopic vision, and provide a stereoscopic image to a user by displaying a parallax image group generated by the workstation 130 on the monitor. The image storage apparatus 120 stores therein volume data generated by the medical image diagnostic apparatus 110, and a parallax image group generated by the workstation 130. For example, the workstation 130 and the terminal apparatus 140 acquire volume data or a parallax image group from the image storage apparatus 120, and applies a given image process to the volume data or the parallax image group thus acquired, or displays the parallax image group on the monitor. Each of these apparatuses will now be explained one by one.

The medical image diagnostic apparatus 110 is, for example, an X-ray diagnostic apparatus, an X-ray computed tomography (CT) apparatus, a magnetic resonance imaging (MRI) apparatus, an ultrasonic diagnostic apparatus, a single-photon emission computed tomography (SPECT) apparatus, a positron emission computed tomography (PET) apparatus, an SPECT-CT apparatus in which a SPECT apparatus and an X-ray CT apparatus are integrated, a PET-CT apparatus in which a PET apparatus and an X-ray CT apparatus are integrated, or a group of these apparatuses. The medical image diagnostic apparatus 110 according to the first embodiment is capable of generating three-dimensional medical image data (volume data).

Specifically, the medical image diagnostic apparatus 110 according to the first embodiment generates volume data by capturing images of a subject. For example, the medical image diagnostic apparatus 110 collects data such as projection data or magnetic resonance (MR) signals by capturing images of a subject, and generates volume data by reconstructing medical image data consisting of a plurality of axial surfaces along a body axis of the subject from the data thus collected. For example, when the medical image diagnostic apparatus 110 reconstructs medical image data consisting of five hundred axial surfaces, the medical image data consisting of the five hundred axial surfaces will be the volume data. The projection data or the MR signals of the subject captured by the medical image diagnostic apparatus 110 themselves may also be used as the volume data.

The medical image diagnostic apparatus 110 according to the first embodiment also transmits the volume data thus generated to the image storage apparatus 120. When the medical image diagnostic apparatus 110 transmits the volume data to the image storage apparatus 120, the medical image diagnostic apparatus 110 transmits a patient ID for identifying a patient, an examination ID for identifying an examination, an apparatus ID for identifying the medical image diagnostic apparatus 110, a series ID for identifying a single image capturing performed by the medical image diagnostic apparatus 110, and the like as well, as additional information.

The image storage apparatus 120 is a database storing therein medical images. Specifically, the image storage apparatus 120 according to the first embodiment receives volume data from the medical image diagnostic apparatus 110, and stores the volume data thus received in a given storage unit. In the first embodiment, the workstation 130 generates a parallax image group from the volume data, and transmits the parallax image group thus generated to the image storage apparatus 120. In response, the image storage apparatus 120 stores the parallax image group transmitted by the workstation 130 in a given storage unit. Alternatively, the embodiment may be an example in which the workstation 130 and the image storage apparatus 120, such as those illustrated in FIG. 1, are integrated, by employing the workstation 130 capable of storing therein a large volume of images. In other words, the embodiment may be an example in which the volume data or the parallax image group is stored locally in the workstation 130.

In the first embodiment, the volume data or the parallax image group stored in the image storage apparatus 120 is stored in a manner associated with a patient ID, an examination ID, an apparatus ID, a series ID, and the like. The workstation 130 or the terminal apparatus 140 is then allowed to perform a retrieval using a patient ID, an examination ID, an apparatus ID, a series ID, and the like, in order to acquire required volume data or a parallax image group from the image storage apparatus 120.

The workstation 130 is an image processing apparatus that performs image processes to a medical image. Specifically, the workstation 130 according to the first embodiment generates a parallax image group by performing various rendering processes to the volume data acquired from the image storage apparatus 120.

The workstation 130 according to the first embodiment includes a monitor capable of providing a stereoscopic vision (also referred to as a stereoscopic display monitor or a stereoscopic image display apparatus) as a display unit. The workstation 130 generates a parallax image group, and displays the parallax image group thus generated on the stereoscopic display monitor. As a result, an operator of the workstation 130 can perform operation for generating a parallax image group while checking a stereoscopic image enabled for a stereoscopic vision and displayed on the stereoscopic display monitor.

The workstation 130 also transmits a parallax image group generated thereby to the image storage apparatus 120 or the terminal apparatus 140. When the workstation 130 transmits a parallax image group to the image storage apparatus 120 or the terminal apparatus 140, the workstation 130 transmits a patient ID, an examination ID, an apparatus ID, a series ID, and the like, as additional information. The additional information transmitted when a parallax image group is transmitted to the image storage apparatus 120 may include additional information related to the parallax image group. The additional information related to the parallax image group includes, for example, the number of parallax images (e.g., "nine"), the resolution of the parallax image (for example, "466 pixels by 350 pixels"), information related to three-dimensional virtual space represented by the volume data from which the parallax image group is generated (volume space information), and information related to the position of the subject data that is the data representing a subject such as an organ included in the volume data (subject position information).

The terminal apparatus 140 is an apparatus for allowing a physician or an examiner who is working in the hospital to view the medical image. For example, the terminal apparatus 140 is, for example, a personal computer (PC), a tablet PC, a personal digital assistant (PDA), or a mobile phone operated by a physician or an examiner who is working in the hospital. Specifically, the terminal apparatus 140 according to the first embodiment includes a stereoscopic display monitor as a display unit. The terminal apparatus 140 acquires a parallax image group from the image storage apparatus 120, and displays the parallax image group thus acquired on the stereoscopic display monitor. As a result, a physician or an examiner who is an observer can view a medical image enabled for a stereoscopic vision. The terminal apparatus 140 may also be an information processing terminal connected to a stereoscopic display monitor that is an external apparatus.

The stereoscopic display monitor included in the workstation 130 or the terminal apparatus 140 will now be explained. A common, general-purpose monitor that is most widely used today displays two-dimensional images two-dimensionally, and is not capable of displaying a two-dimensional image stereoscopically. If an observer requests a stereoscopic vision on the general-purpose monitor, an apparatus outputting images to the general-purpose monitor needs to display two-parallax images in parallel that can be stereoscopically perceived by the observer, using a parallel technique or a crossed-eye technique. Alternatively, the apparatus outputting images to the general-purpose monitor needs to present images that can be stereoscopically perceived by the observer using anaglyph, which uses a pair of glasses having a red filter for the left eye and a blue filter for the right eye, for example.

Some stereoscopic display monitors enable two parallax images (also referred to as binocular parallax images) to be stereoscopically perceived, by using special equipment such as a pair of stereoscopic glasses.

Figure 2A:
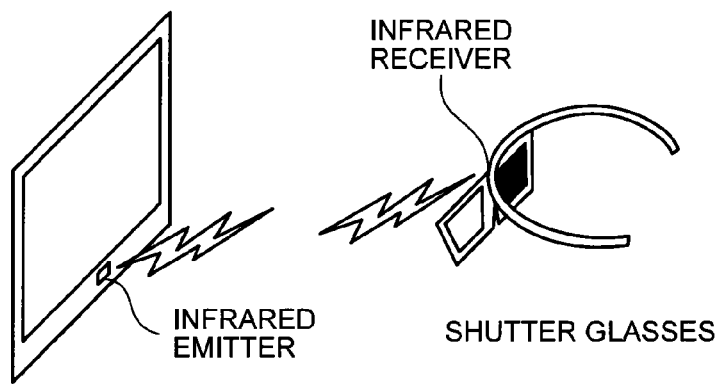
FIG. 2A is a schematic (1) for explaining an example of a stereoscopic display monitor providing a stereoscopic vision using two-parallax images.
Figure 2B:
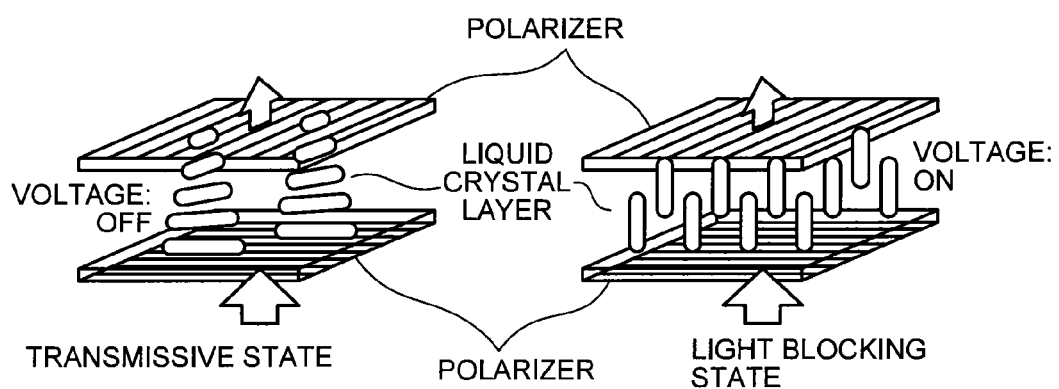
FIG. 2B is a schematic (2) for explaining the example of the stereoscopic display monitor providing a stereoscopic vision using two-parallax images.

FIGS. 2A and 2B are schematics for explaining an example of a stereoscopic display monitor providing a stereoscopic vision using two-parallax images. The example illustrated in FIGS. 2A and 2B is a stereoscopic display monitor providing a stereoscopic vision using a shutter technique. In this example, a pair of shutter glasses are used as stereoscopic glasses worn by an observer who observes the monitor. The stereoscopic display monitor outputs two-parallax images to the monitor alternately. For example, the monitor illustrated in FIG. 2A outputs an image for the left eye and an image for the right eye alternately at 120 hertz. An infrared emitter is installed in the monitor, as illustrated in FIG. 2A, and the infrared emitter controls infrared outputs based on the timing at which the images are swapped.

The infrared output from the infrared emitter is received by an infrared receiver provided on the shutter glasses illustrated in FIG. 2A. A shutter is installed on the frame on each side of the shutter glasses. The shutter glasses switch the right shutter and the left shutter between a transmissive state and a light-blocking state alternately, based on the timing at which the infrared receiver receives infrared. A process of switching the shutters between the transmissive state and the light-blocking state will now be explained.

As illustrated in FIG. 2B, each of the shutters includes an incoming polarizer and an outgoing polarizer, and also includes a liquid crystal layer interposed between the incoming polarizer and the outgoing polarizer. The incoming polarizer and the outgoing polarizer are orthogonal to each other, as illustrated in FIG. 2B. In an "OFF" state during which a voltage is not applied as illustrated in FIG. 2B, the light having passed through the incoming polarizer is rotated by 90 degrees by the effect of the liquid crystal layer, and thus passes through the outgoing polarizer. In other words, a shutter with no voltage applied is in the transmissive state.

By contrast, as illustrated in FIG. 2B, in an "ON" state during which a voltage is applied, the polarization rotation effect of liquid crystal molecules in the liquid crystal layer is lost. Therefore, the light having passed through the incoming polarizer is blocked by the outgoing polarizer. In other words, the shutter applied with a voltage is in the light-blocking state.

The infrared emitter outputs infrared for a time period while which an image for the left eye is displayed on the monitor, for example. During the time the infrared receiver is receiving infrared, no voltage is applied to the shutter for the left eye, while a voltage is applied to the shutter for the right eye. In this manner, as illustrated in FIG. 2A, the shutter for the right eye is switched to the light-blocking state and the shutter for the left eye is switched to the transmissive state, thus allowing the image for the left eye to enter the left eye of the observer. For a time period while which an image for the right eye is displayed on the monitor, the infrared emitter stops outputting infrared. When the infrared receiver receives no infrared, a voltage is applied to the shutter for the left eye, while no voltage is applied to the shutter for the right eye. In this manner, the shutter for the left eye is switched to the light-blocking state, and the shutter for the right eye is switched to the transmissive state, thus allowing the image for the right eye to enter the right eye of the observer. As explained above, the stereoscopic display monitor illustrated in FIGS. 2A and 2B provides a stereoscopic image enabled to be stereoscopically perceived by the observer, by switching the states of the shutters in association with the images displayed on the monitor. As a stereoscopic display monitor being capable of enabling two-parallax image to be stereoscopically perceived, a monitor adopting a technique using a polarizer glasses are also known, in addition to the shutter technique explained above.

Some stereoscopic display monitors that have recently been put into practical use allow multiple parallax images, e.g., nine-parallax images, to be stereoscopically viewed by an observer with the naked eyes, by adopting a light ray controller such as a lenticular lens. Such a stereoscopic display monitor enables stereoscopy using the binocular parallax, and also enables stereoscopy using moving parallax, where a movie observed by an observer changes following the movement of the observer's viewpoint.

Figure 3:
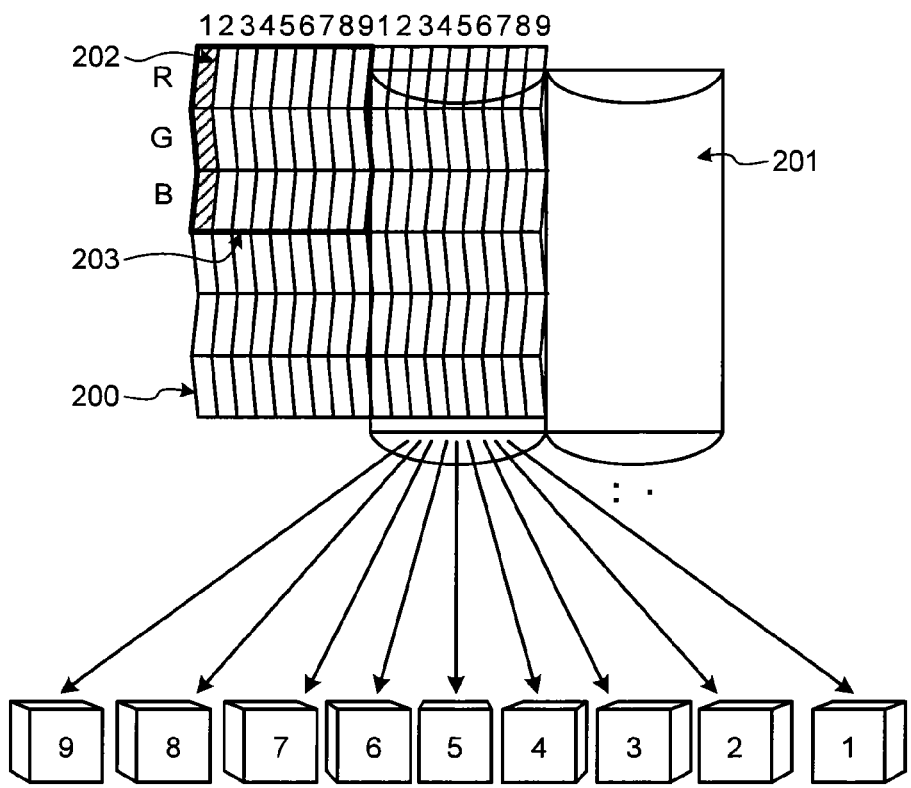
FIG. 3 is a schematic for explaining an example of a stereoscopic display monitor providing a stereoscopic vision using nine-parallax images.

FIG. 3 is a schematic for explaining an example of a stereoscopic display monitor providing a stereoscopic vision using nine-parallax images. In the stereoscopic display monitor illustrated in FIG. 3, a light ray controller is arranged on the front surface of a flat display screen 200 such as a liquid crystal panel. In the stereoscopic display monitor illustrated in FIG. 3, for example, a vertical lenticular sheet 201 having an optical aperture extending in a vertical direction is fitted on the front surface of the display screen 200 as a light ray controller. Although the vertical lenticular sheet 201 is fitted so that the convex of the vertical lenticular sheet 201 faces the front side in the example illustrated in FIG. 3, the vertical lenticular sheet 201 may be also fitted so that the convex faces the display screen 200.

As illustrated in FIG. 3, the display screen 200 has pixels 202 that are arranged in a matrix. Each of the pixels 202 has an aspect ratio of 3:1, and includes three sub-pixels of red (R), green (G), and blue (B) that are arranged vertically. The stereoscopic display monitor illustrated in FIG. 3 converts nine-parallax images consisting of nine images into an intermediate image in a given format (e.g., a grid-like format), and outputs the result to the display screen 200. In other words, the stereoscopic display monitor illustrated in FIG. 3 assigns and outputs nine pixels located at the same position in the nine-parallax images to the pixels 202 arranged in nine columns. The pixels 202 arranged in nine columns function as a unit pixel group 203 that displays nine images from different viewpoint positions at the same time.

The nine-parallax images simultaneously output as the unit pixel group 203 to the display screen 200 are radiated with a light emitting diode (LED) backlight, for example, as parallel rays, and travel further in multiple directions through the vertical lenticular sheet 201. Light for each of the pixels included in the nine-parallax images is output in multiple directions, whereby the light entering the right eye and the left eye of the observer changes as the position (viewpoint position) of the observer changes. In other words, depending on the angle from which the observer perceives, the parallax image entering the right eye and the parallax image entering the left eye have different parallax angles. Therefore, the observer can perceive a captured object stereoscopically from any one of the nine positions illustrated in FIG. 3, for example. At the position "5" illustrated in FIG. 3, the observer can perceive the captured object stereoscopically in an orientation in which the object faces directly the observer. At each of the positions other than the position "5" illustrated in FIG. 3, the observer can perceive the captured object stereoscopically in different orientations. The stereoscopic display monitor illustrated in FIG. 3 is merely an example. The stereoscopic display monitor for displaying nine-parallax images may be a liquid crystal with horizontal stripes of "RRR . . . , GGG . . . , BBB . . . " as illustrated in FIG. 3, or a liquid crystal with vertical stripes of "RGBRGB . . . ". The stereoscopic display monitor illustrated in FIG. 3 may be a monitor using a vertical lens in which the lenticular sheet is arranged vertically as illustrated in FIG. 3, or a monitor using a diagonal lens in which the lenticular sheet is arranged diagonally.

An exemplary configuration of the image processing system 1 according to the first embodiment is briefly explained above. Applications of the image processing system 1 described above are not limited to a system in which a PACS is installed. For example, the image processing system 1 may be applied in the same manner to a system installed with an electronic medical record system for managing electronic medical records with attachments of medical images. In such an installation, the image storage apparatus 120 is a database storing therein electronic medical records. The image processing system 1 may also be applied in the same manner to a system in which a hospital information system (HIS) or a radiology information system (RIS) is installed, for example. Furthermore, the image processing system 1 is not limited to the exemplary configuration explained above. Functions provided to each of the apparatuses and distributions of the functions among the apparatuses may be changed as appropriate, depending on how the system is operated.

Figure 4:
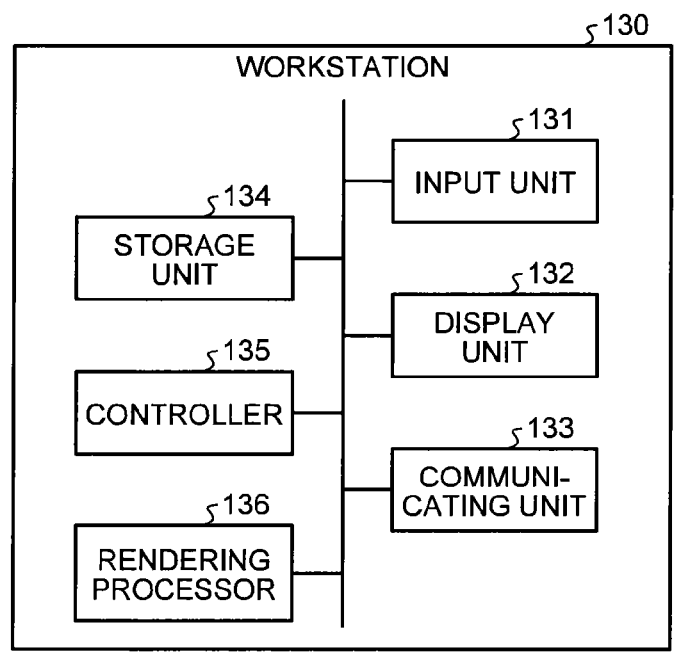
FIG. 4 is a schematic for explaining an exemplary configuration of a workstation according to the first embodiment.

An exemplary configuration of the workstation according to the first embodiment will now be explained with reference to FIG. 4. FIG. 4 is a schematic for explaining an exemplary configuration of the workstation according to the first embodiment. In the explanation below, a "parallax image group" means a group of images for a stereoscopic vision, and is generated by applying a volume rendering process to volume data. A "parallax image" means each of the images included in a "parallax image group". In other words, a "parallax image group" consists of a plurality of "parallax images" each having a different viewpoint position.

The workstation 130 according to the first embodiment is a high-performance computer suitable for applications such as image processing, and includes an input unit 131, a display unit 132, a communicating unit 133, a storage unit 134, a controller 135, and a rendering processor 136, as illustrated in FIG. 4. In the explanation below, the workstation 130 is explained to be a high-performance computer suitable for applications such as image processing, but is not limited thereto. The workstation 130 may be any type of information processing apparatuses, and may be any type of personal computers, for example.

The input unit 131 is a mouse, a keyboard, a trackball, or the like, and receives inputs of various operations for the workstation 130 from an operator. Specifically, the input unit 131 according to the first embodiment receives inputs of information for acquiring volume data to be applied with a rendering process from the image storage apparatus 120. For example, the input unit 131 receives inputs of a patient ID, an examination ID, an apparatus ID, and a series ID, for example. The input unit 131 according to the first embodiment also receives inputs of conditions related to the rendering process (hereinafter referred to as a rendering condition).

The display unit 132 is a liquid crystal panel, for example, as a stereoscopic display monitor, and displays various types of information. Specifically, the display unit 132 according to the first embodiment displays a graphical user interface (GUI) for receiving various operations from an operator, a parallax image group, and the like. The communicating unit 133 is a network interface card (NIC), for example, and establishes communications with other apparatuses.

The storage unit 134 is a hard disk, a semiconductor memory element, and the like, and stores therein various types of information. Specifically, the storage unit 134 according to the first embodiment stores therein volume data acquired from the image storage apparatus 120 via the communicating unit 133. The storage unit 134 according to the first embodiment also stores therein volume data applied with a rendering process, and a parallax image group generated by the rendering process, for example.

The controller 135 is an electronic circuit such as a central processing unit (CPU), a micro processing unit (MPU), or a graphics processing unit (GPU), or an integrated circuit such as an application specific integrated circuit (ASIC) or a field programmable gate array (FPGA), and controls the entire workstation 130.

For example, the controller 135 according to the first embodiment controls to display a GUI or a parallax image group on the display unit 132. For example, the controller 135 also controls transmissions and receptions of volume data or a parallax image group to and from the image storage apparatus 120 via the communicating unit 133. For example, the controller 135 also controls a rendering process performed by the rendering processor 136. For example, the controller 135 also controls to read volume data from the storage unit 134, and to store a parallax image group in the storage unit 134.

The rendering processor 136 applies various rendering processes to volume data acquired from the image storage apparatus 120, and generates a parallax image group under the control of the controller 135. Specifically, the rendering processor 136 according to the first embodiment reads volume data from the storage unit 134, and applies a pre-process to the volume data. The rendering processor 136 then generate a parallax image group by applying a volume rendering process to the volume data applied with the pre-process. The rendering processor 136 then generates a two-dimensional image in which various types of information (e.g., a scale, a patient name, and a checkup item) are represented, and superimposes the two-dimensional image over each one of the parallax image group to generate two-dimensional images to be output. The rendering processor 136 stores the parallax image group and the two-dimensional images to be output thus generated in the storage unit 134. In the first embodiment, a rendering process means the entire image processing applied to the volume data. A volume rendering process, which is included in the rendering process, means a process of generating a two-dimensional image reflected with three-dimensional information. A medical image generated in the rendering process corresponds to a parallax image, for example.

Figure 5:
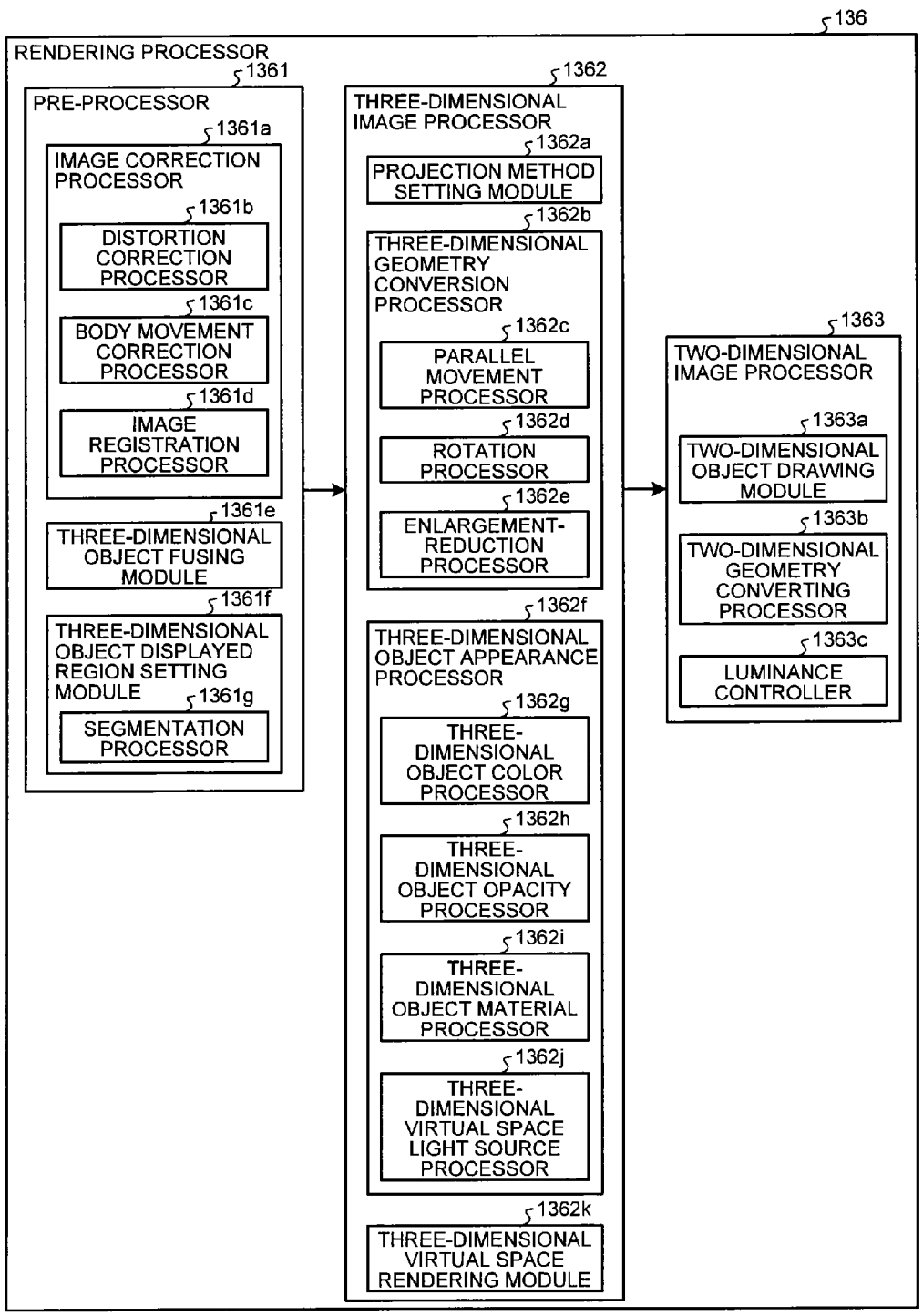
FIG. 5 is a schematic for explaining an exemplary configuration of a rendering processor illustrated in FIG. 4.

FIG. 5 is a schematic for explaining an exemplary configuration of the rendering processor illustrated in FIG. 4. As illustrated in FIG. 5, the rendering processor 136 includes a pre-processor 1361, a three-dimensional image processor 1362, and a two-dimensional image processor 1363. The pre-processor 1361 applies a pre-process to the volume data. The three-dimensional image processor 1362 generates a parallax image group from the volume data applied with the pre-process. The two-dimensional image processor 1363 generates a two-dimensional image to be output in which the various types of information are superimposed over the parallax image group. Each of these components will be described below.

The pre-processor 1361 is a processing unit for applying various pre-processes to the volume data when the rendering process is applied to the volume data, and includes an image correction processor 1361*a*, a three-dimensional object fusing module 1361*e*, a three-dimensional object displayed region setting module 1361*f*.

The image correction processor 1361*a* is a processing unit for performing an image correcting process before handling two types of volume data as a single piece of volume data, and includes a distortion correction processor 1361*b*, a body movement correction processor 1361*c*, and an image registration processor 1361*d*, as illustrated in FIG. 5. For example, the image correction processor 1361*a* performs an image correcting process when volume data of a PET image and volume data of an X-ray CT image both of which are generated by a PET-CT apparatus are to be handled as a single piece of data. As another example, the image correction processor 1361*a* performs an image correcting process when volume data of a T1 emphasized image and volume data of a T2 emphasized image both of which are generated by an MRI apparatus are to be handled as a single piece of volume data.

The distortion correction processor 1361*b* corrects distortion in each piece of volume data caused by collection conditions under which the data is collected by the medical image diagnostic apparatus 110. The body movement correction processor 1361*c* corrects a movement in data caused by a body movement of the subject occurred when the data used in generating each piece of volume data is collected. The image registration processor 1361*d* performs registration between two pieces of volume data applied with the correcting processes performed by the distortion correction processor 1361*b* and the body movement correction processor 1361*c*, using a cross correlation method, for example.

The three-dimensional object fusing module 1361*e* fuses the pieces of volume data registered with respect to each other by the image registration processor 1361*d*. The processes performed by the image correction processor 1361*a* and the three-dimensional object fusing module 1361*e* are omitted when the rendering process is performed to a single piece of volume data.

The three-dimensional object displayed region setting module 1361*f* is a processing unit for defining a region to be displayed corresponding to an organ to be displayed designated by an operator, and includes a segmentation processor 1361*g*. The segmentation processor 1361*g* is a processing unit for extracting an organ such as a heart, a lung, or a blood vessel designated by an operator, by performing region growing, for example, based on pixel values (voxel values) in the volume data, for example.

When any organ to be displayed is not designated by an operator, the segmentation processor 1361*g* does not perform the segmenting process. When an operator specifies an organ to be displayed in plurality, the segmentation processor 1361*g* extracts these organs. The process performed by the segmentation processor 1361*g* may be performed again when an operator looking at the rendering image makes a request for fine adjustment.

The three-dimensional image processor 1362 performs a volume rendering process to the volume data applied with the pre-process of the pre-processor 1361. The three-dimensional image processor 1362 includes a projection method setting module 1362*a*, a three-dimensional geometry conversion processor 1362*b*, a three-dimensional object appearance processor 1362*f*, and a three-dimensional virtual space rendering module 1362*k*, as processing units for performing a volume rendering process.

The projection method setting module 1362*a* determines a projection method used in generating a parallax image group. For example, the projection method setting module 1362*a* determines if the volume rendering process is to be performed using parallel projection, or performed using perspective projection.

The three-dimensional geometry conversion processor 1362b is a processing unit for determining information for three-dimensional-geometrically converting the volume data to be applied with the volume rendering process, and includes a parallel movement processor 1362c, a rotation processor 1362d, and an enlargement-reduction processor 1362e. The parallel movement processor 1362c is a processing unit for determining the amount of movement by which the volume data is to be moved in parallel when the viewpoint position used in the volume rendering process is moved in parallel. The rotation processor 1362d is a processing unit for determining the amount of movement by which the volume data is to be moved rotationally when the viewpoint position used in the volume rendering process is moved rotationally. The enlargement-reduction processor 1362e is a processing unit for determining an enlargement ratio or a reduction ratio of the volume data when an enlargement or a reduction of the parallax image group is requested.

The three-dimensional object appearance processor 1362f includes a three-dimensional object color processor 1362g, a three-dimensional object opacity processor 1362h, a three-dimensional object material processor 1362i, and a three-dimensional virtual space light source processor 1362j. The three-dimensional object appearance processor 1362f performs a process of determining conditions for displaying a parallax image group to be displayed using these processing units, based on an operator request, for example.

The three-dimensional object color processor 1362g is a processing unit for determining the color applied to each of the regions segmented in the volume data. The three-dimensional object opacity processor 1362h is a processing unit for determining opacity of each voxel included in each of the regions in the volume data. A region behind another region in which the opacity is set to "100 percent" in the volume data is not represented in a parallax image group. A region in which the opacity is set to "0 percent" in the volume data is not represented as well in a parallax image group.

The three-dimensional object material processor 1362i is a processing unit for adjusting the texture in which each of the regions segmented in the volume data is represented, by determining a material for each segment in the volume data. The three-dimensional virtual space light source processor 1362j is a processing unit for determining the position of a virtual light source or the type of the virtual light source set in the three-dimensional virtual space before applying a volume rendering process to the volume data. Examples of types of the virtual light source include a light source emitting parallel light rays from the infinity, and a light source emitting radial light rays from a viewpoint.

The three-dimensional virtual space rendering module 1362k generates a parallax image group by applying a volume rendering process to the volume data. In performing a volume rendering process, the three-dimensional virtual space rendering module 1362k uses various types of information determined by the projection method setting module 1362a, the three-dimensional geometry conversion processor 1362b, and the three-dimensional object appearance processor 1362f.

The three-dimensional virtual space rendering module 1362k performs a volume rendering process in accordance with rendering conditions. An example of the rendering condition is "parallel projection" or "perspective projection". Other examples of the rendering condition include "a reference viewpoint position and a parallax angle". Other examples of the rendering condition include "a parallel movement of the viewpoint position", "a rotational movement of the viewpoint position", "an enlargement of the parallax image group", and "a reduction of the parallax image group". Other examples of the rendering condition include "a color to be applied", "transparency", "the texture", "the position of the virtual light source", and "the type of the virtual light source". Such rendering conditions may be received from an operator via the input unit 131, or preconfigured as an initial setting. In either case, the three-dimensional virtual space rendering module 1362k receives rendering conditions from the controller 135, and applies a volume rendering process to the volume data in accordance with the rendering conditions. The projection method setting module 1362a, the three-dimensional geometry conversion processor 1362b, and the three-dimensional object appearance processor 1362f determine various types of information required in the rendering conditions, and the three-dimensional virtual space rendering module 1362k generates a parallax image group using the various types of information.

Figure 6:
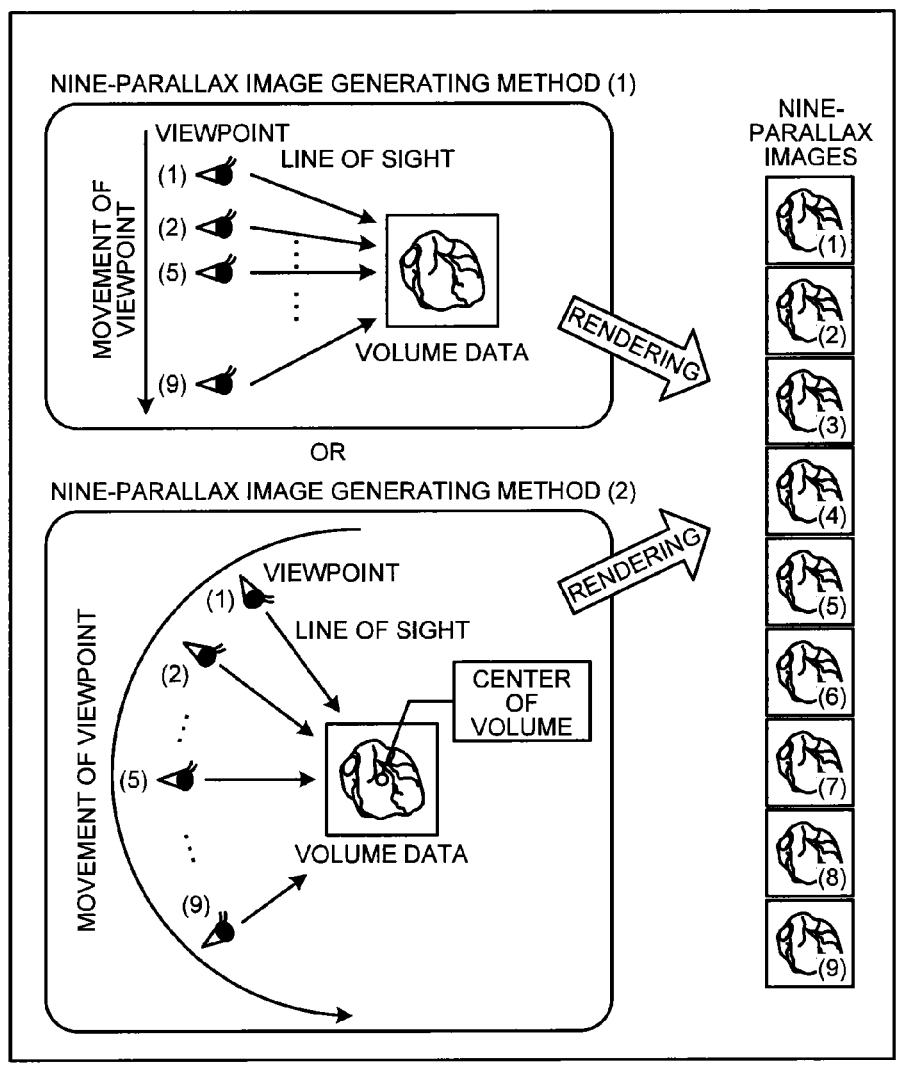
FIG. 6 is a schematic for explaining an example of a volume rendering process according to the first embodiment.

FIG. 6 is a schematic for explaining an example of the volume rendering process according to the first embodiment. For example, it is assumed herein that the three-dimensional virtual space rendering module 1362k receives parallel projection, and further receives a reference viewpoint position (5) and a parallax angle of "one degree" as rendering conditions, as illustrated in a "nine-parallax image generating method (1)" in FIG. 6. In such a case, the three-dimensional virtual space rendering module 1362k generates nine parallax images, each having a parallax angle (angle between the lines of sight) shifted by one degree, by parallel projection, by moving the viewpoint position from (1) to (9) in such a way that the parallax angle is set in every "one degree". Before performing parallel projection, the three-dimensional virtual space rendering module 1362k sets a light source radiating parallel light rays from the infinity along the line of sight.

As another example, it is assumed that the three-dimensional virtual space rendering module 1362k receives perspective projection, and further receives a reference viewpoint position (5) and a parallax angle of "one degree" as rendering conditions, as illustrated in "nine-parallax image generating method (2)" in FIG. 6. In such a case, the three-dimensional virtual space rendering module 1362k generates nine parallax images, each having a parallax angle shifted by one degree, by perspective projection, by moving the viewpoint position from (1) to (9) around the center (the center of gravity) of the volume data in such a way that the parallax angle is set in every "one degree". Before performing perspective projection, the three-dimensional virtual space rendering module 1362k sets a point light source or a surface light source radiating light three-dimensionally about the line of sight, for each of the viewpoints. Alternatively, when perspective projection is to be performed, the viewpoints (1) to (9) may be shifted in parallel depending on rendering conditions.

The three-dimensional virtual space rendering module 1362k may also perform a volume rendering process using both parallel projection and perspective projection, by setting a light source radiating light two-dimensionally, radially centering on the line of sight for the vertical direction of the volume rendering image to be displayed, and radiating parallel light rays from the infinity along the line of sight for the horizontal direction of the volume rendering image to be displayed.

The nine parallax images thus generated correspond to a parallax image group. In the first embodiment, the controller 135 then converts these nine parallax images into an intermediate image in which these parallax images are arranged in a predetermined format (e.g., a grid-like format), for example, and the intermediate image is output to the display unit 132 being a stereoscopic display monitor. An operator of the workstation 130 is then allowed to make operations for generating a parallax image group while checking a stereoscopic medical image displayed on the stereoscopic display monitor.

Explained in the example illustrated in FIG. 6 is an example in which a projection method, a reference viewpoint position, and a parallax angle are received as rendering conditions. When other conditions are received as rendering conditions, the three-dimensional virtual space rendering module 1362*k* generates a parallax image group reflected with each of the rendering conditions.

The three-dimensional virtual space rendering module 1362*k* not only has a function of performing a volume rendering, but also has a function of reconstructing a multiplaner reconstruction (MPR) image by performing a multiplaner reconstruction. The three-dimensional virtual space rendering module 1362*k* also has a function of performing a "curved MPR" and a function of performing "intensity projection".

The parallax image group generated from the volume data by the three-dimensional image processor 1362 is used as an underlay. An overlay in which various types of information (e.g., a scale, a patient name, and a checkup item) are represented is superimposed over the underlay, whereby creating a two-dimensional image to be output. The two-dimensional image processor 1363 is a processing unit for generating a two-dimensional image to be output by performing image processes to the overlay and the underlay, and includes a two-dimensional object drawing module 1363*a*, a two-dimensional geometry converting processor 1363*b*, and a luminance controller 1363*c*, as illustrated in FIG. 5. For example, the two-dimensional image processor 1363 generates nine two-dimensional images to be output by superimposing a single overlay to each one of nine parallax images (underlays), so that the load required in the process of generating two-dimensional image to be output is reduced. In the explanation below, an underlay on which an overlay is superimposed is sometimes simply referred to as a "parallax image".

The two-dimensional object drawing module 1363*a* is a processing unit for drawing various types of information that is to be represented in the overlay. The two-dimensional geometry converting processor 1363*b* is a processing unit that applies a process of moving the position of the various types of information represented in the overlay in parallel or rotationally, and a process of enlarging or reducing the various types of information represented in the overlay.

The luminance controller 1363*c* is a processing unit for performing a luminance conversion process, and is a processing unit for adjusting the luminance of the overlay and the underlay in accordance with the gradation of the stereoscopic display monitor over which the parallax images are output, and in accordance with parameters for image processes such as the window width (WW) and the window level (WL), for example.

The controller 135 stores the two-dimensional images to be output thus generated in the storage unit 134, and transmits the two-dimensional images to be output to the image storage apparatus 120 via the communicating unit 133, for example. The terminal apparatus 140 then acquires two-dimensional images to be output from the image storage apparatus 120, converts the two-dimensional images to be output into an intermediate image in which these two-dimensional images are arranged in a given format (e.g., a grid-like format), and displays the intermediate image on the stereoscopic display monitor, for example. Alternatively, the controller 135 stores the two-dimensional images to be output in the storage unit 134, transmits the two-dimensional images to be output not only to the image storage apparatus 120 but also to the terminal apparatus 140 via the communicating unit 133. The terminal apparatus 140 then converts the two-dimensional images to be output received from the workstation 130 into an intermediate image in which these two-dimensional images are arranged in a given format (e.g., a grid-like format), and displays the intermediate image on a stereoscopic display monitor, for example. In this manner, a physician or an examiner using the terminal apparatus 140 can view a stereoscopic medical image in which various types of information (e.g., a scale, a patient name, and a checkup item) are represented.

As described above, the terminal apparatus 140 displays a stereoscopic image that can be stereoscopically perceived by an observer on a stereoscopic display monitor using a plurality of parallax images. At this time, the terminal apparatus 140 displays a cursor, which can be operated using a pointing device such as a mouse, along with the stereoscopic image. Such a cursor can be moved three-dimensionally within a three-dimensional space where the stereoscopic image is displayed (hereinafter also referred to as a "stereoscopic image space"). For example, an observer specifies a region of interest (ROI) by moving a cursor and designating a given region in the stereoscopic image. A stereoscopic image space is generally is formed as a space representing a space in front of and behind the display surface of a stereoscopic display monitor 142.

Figure 7:
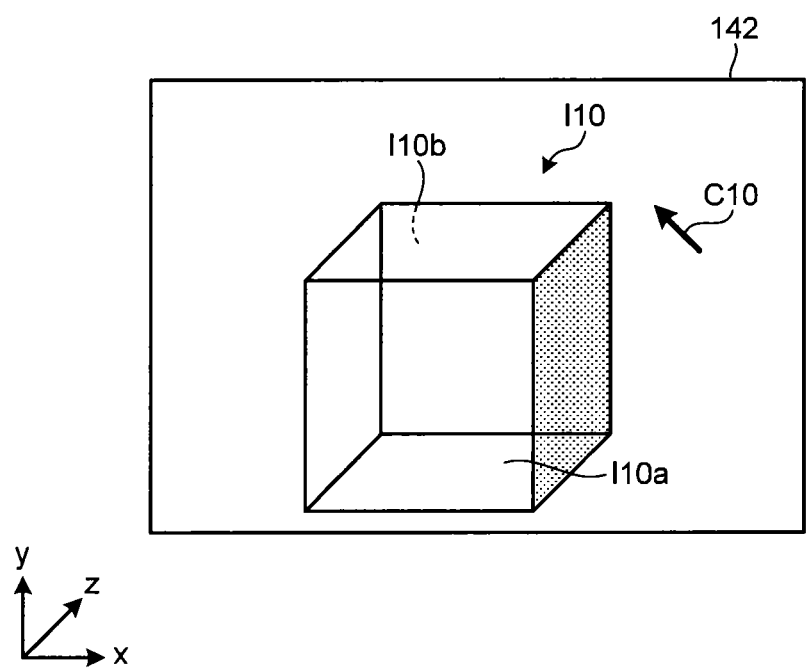
FIG. 7 is a schematic illustrating an example of a stereoscopic image displayed on a stereoscopic display monitor.

There are some cases where an observer has difficulty recognizing the depth-direction position of the cursor displayed along with a stereoscopic image. This point will now be explained specifically with reference to FIG. 7. FIG. 7 is a schematic illustrating an example of a stereoscopic image displayed on a stereoscopic display monitor. In the example illustrated in FIG. 7, a cursor C10 and a stereoscopic image I10 are displayed on the stereoscopic display monitor 142 provided to the terminal apparatus 140. Although the stereoscopic image I10 is illustrated three-dimensionally on a two-dimensional surface in FIG. 7, FIG. 7 suggests that the stereoscopic image I10 is displayed stereoscopically in a stereoscopic image space that is a three-dimensional space.

As illustrated in the example in FIG. 7, the position of the cursor C10 in the depth direction (in the z-direction in FIG. 7) of a stereoscopic image space is difficult to recognize when the stereoscopic image I10 and the cursor C10 are displayed on the stereoscopic display monitor 142. For example, the cursor C10 illustrated in FIG. 7 can be perceived as being displayed at a position between a front surface I10*a* and a rear surface I10*b* of the stereoscopic image I10, as being displayed in front of the front surface I10*a* (in a direction moving closer to the observer), or as being displayed further behind the rear surface I10*b* (in a direction moving away from the observer). In this manner, the observer has difficulty recognizing the position of the cursor C10.

In response to this issue, the terminal apparatus 140 in the first embodiment generates an image of a given graphic indicating the position of the cursor in the depth direction in a stereoscopic image space, and superimposes the graphic image over a plurality of parallax images generated by the rendering processor 136, before displaying the parallax images on the stereoscopic display monitor 142. In this manner, the terminal apparatus 140 in the first embodiment enables the observer to recognize the position of the cursor in the depth direction.

Figure 8:
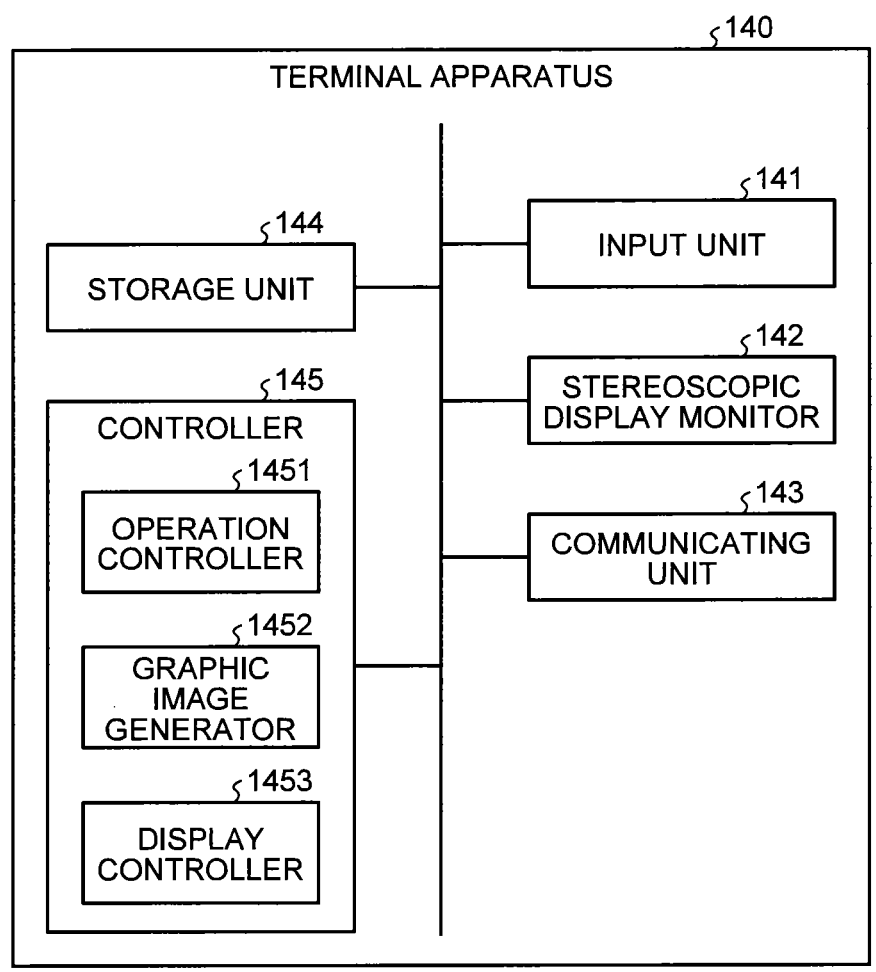
FIG. 8 is a schematic for explaining an exemplary configuration of a terminal apparatus in the first embodiment.

The terminal apparatus 140 in the first embodiment will be explained below in detail. FIG. 8 is a schematic for explaining an exemplary configuration of the terminal apparatus 140 in the first embodiment. As illustrated in the example in FIG. 8, the terminal apparatus 140 in the first embodiment includes an input unit 141, the stereoscopic display monitor 142, a communicating unit 143, a storage unit 144, and a controller 145.

The input unit 141 is a pointing device such as a mouse or a trackball, or an information input device such as a keyboard, and receives inputs of various operations to the terminal apparatus 140 from an operator. For example, the input unit 141 receives inputs such as a patient ID, an examination ID, an apparatus ID, and a series ID for designating volume data requested to be stereoscopically displayed by the operator, as a stereoscopic vision request. The input unit 141 also receives an operation for moving a cursor displayed on the stereoscopic display monitor 142 via a mouse, for example.

The stereoscopic display monitor 142 is a liquid crystal panel, for example, being a stereoscopic display monitor, and displays various types of information. Specifically, the stereoscopic display monitor 142 according to the first embodiment displays a GUI for receiving various operations from an operator, a parallax image group, and the like. For example, the stereoscopic display monitor 142 is a stereoscopic display monitor explained with reference to FIGS. 2A and 2B (hereinafter referred to as a two-parallax monitor), or a stereoscopic display monitor explained with reference to FIG. 6 (hereinafter referred to as a nine parallax monitor). Explained below is an example in which the stereoscopic display monitor 142 is a nine parallax monitor.

The communicating unit 143 is a NIC, for example, and establishes communications with other apparatuses. Specifically, the communicating unit 143 according to the first embodiment transmits a stereoscopic vision request received by the input unit 141 to the image storage apparatus 120. The communicating unit 143 according to the first embodiment also receives a parallax image group transmitted by the image storage apparatus 120, in response to a stereoscopic vision request.

The storage unit 144 is a hard disk, a semiconductor memory element, and the like, and stores therein various types of information. Specifically, the storage unit 144 according to the first embodiment stores therein the parallax image group acquired from the image storage apparatus 120 via the communicating unit 143. The storage unit 144 also stores therein additional information of the parallax image group (e.g., a parallax number, resolution, volume space information, and subject position information) acquired from the image storage apparatus 120 via the communicating unit 143.

The controller 145 is an electronic circuit such as a CPU, an MPU, and a GPU, or an integrated circuit such as an ASIC and an FPGA, and controls the entire terminal apparatus 140. For example, the controller 145 controls transmitting and receiving a stereoscopic vision request or a parallax image group to and from the image storage apparatus 120 via the communicating unit 143. As another example, the controller 145 controls storing a parallax image group in the storage unit 144, and reading a parallax image group from the storage unit 144. As another example, the controller 145 superimposes an image (overlay) of a cursor operable using the input unit 141 such as a pointing device over a parallax image group (underlay) received from the image storage apparatus 120.

As illustrated in the example in FIG. 8, the controller 145 includes an operation controller 1451, a graphic image generator 1452, and a display controller 1453, and enables a depth-direction position pointed by the cursor to be recognized more easily, through processes performed by these processing units.

The operation controller 1451 performs various processes based on various operations received by the input unit 141. For example, when the input unit 141 receives an input of a stereoscopic vision request, the operation controller 1451 transmits a stereoscopic vision request to the workstation 130 via the communicating unit 143.

When the input unit 141 such as a pointing device is operated, the operation controller 1451 controls the position of the cursor displayed on the stereoscopic display monitor 142. The operation controller 1451 in the first embodiment manages the three-dimensional position of the cursor in a three-dimensional space represented by the same coordinate system as the volume data from which the parallax image group is generated. Hereinafter, the three-dimensional space in which the three-dimensional position of the cursor is managed by the operation controller 1451 is sometimes referred to as a "cursor virtual space".

Specifically, as mentioned earlier, the terminal apparatus 140 acquires volume space information related to the three-dimensional space represented by the volume data from which the parallax image group is generated, from the image storage apparatus 120, as additional information related to the parallax image group. The operation controller 1451 manages the three-dimensional position of the cursor in a cursor virtual space represented by the same coordinate system as the three-dimensional space represented by the volume space information. The operation controller 1451 then moves the cursor in the cursor virtual space when an operation for moving the cursor is performed using the input unit 141. As to be described later, the display controller 1453 generates three-dimensional image data by plotting an image of the cursor in the cursor virtual space, and generates an overlay that is an image of the cursor from the three-dimensional image data thus generated. The operation controller 1451 then superimposes the overlay over the parallax image group, and controls to display the result on the stereoscopic display monitor 142.

The graphic image generator 1452 generates a graphic image that is an image of a given graphic indicating the position of the cursor operable with the input unit 141 in the stereoscopic image space in which the stereoscopic image is displayed on the stereoscopic display monitor 142. The graphic image generated by the graphic image generator 1452 in the first embodiment includes an image of the cursor and a graphic image representing the position of the cursor in the depth direction. This "graphic image" will be used as an overlay to be superimposed over a parallax image group (underlay) acquired from the image storage apparatus 120.

The process performed by the graphic image generator 1452 will now be explained specifically. To begin with, the graphic image generator 1452 acquires the position of the cursor in the cursor virtual space from the operation controller 1451. The graphic image generator 1452 plots the image data of the cursor to the position thus acquired in the cursor virtual space, and plots the image data of a graphic indicating the position of the cursor to a given position in the cursor virtual space, whereby generating "three-dimensional graphic data" that is three-dimensional image data. The graphic image generator 1452 then generates a plurality of graphic images by performing a volume rendering process to the three-dimensional graphic data from a plurality of viewpoint positions. Upon performing the volume rendering process, the graphic image generator 1452 uses the same viewpoint positions as those used in generating the parallax image group. For example, the rendering processor 136 generates a plurality of parallax images by performing a rendering process from a plurality of viewpoint positions that are different relatively with respect to the volume data, e.g., by rotating the volume data while keeping the viewpoint positions and the line of sight fixed, or by changing the viewpoint positions and the line of sight while keeping the volume data fixed. The graphic image generator 1452 performs the volume rendering process to the three-dimensional graphic data from a plurality of viewpoint positions that are different relatively with respect to the three-dimensional graphic data, in the same manner as the viewpoint positions used by the rendering processor 136 in generating the parallax image group.

The graphic image generator 1452 in the first embodiment generates three-dimensional graphic data by plotting image data of a line, a two-dimensional plane, or the like as a graphic indicating the cursor position, on a plane at the same depth-direction position as the cursor in the cursor virtual space.

Specifically, the graphic image generator 1452 identifies a region where subject data is present in the three-dimensional virtual space in which the volume data, from which the parallax image group is generated, is placed, based on the subject position information acquired from the image storage apparatus 120, and identifies a region of the cursor virtual space corresponding to the region thus identified. In other words, although the cursor virtual space has no subject data, the graphic image generator 1452 identifies a region corresponding to the region where the subject data is present in the cursor virtual space, using the subject position information.

The graphic image generator 1452 in the first embodiment then generates three-dimensional graphic data by plotting image data of a line connecting the region where the subject data is present and a position pointed by the cursor on a plane at the same depth-direction position as the cursor in the cursor virtual space, for example. Alternatively, the graphic image generator 1452 generates the three-dimensional graphic data by plotting image data of a two-dimensional plane including a part of or the entire region where the subject data is present and the position pointed by the cursor on a plane at the same depth-direction position as the cursor in the cursor virtual space, for example. The graphic image generator 1452 in the first embodiment then generates a plurality of graphic images by performing a volume rendering process to the three-dimensional graphic data including the image data of the line or the two-dimensional plane.

The display controller 1453 superimposes the graphic images generated by the graphic image generator 1452 over the parallax image group acquired from the image storage apparatus 120, and displays superimposed images in which these images are superimposed on the stereoscopic display monitor 142. Specifically, the display controller 1453 generates superimposed images in which, over the parallax images generated by the rendering processor 136, the respective graphic images generated by the graphic image generator 1452 and having a matched viewpoint position are superimposed. The display controller 1453 then displays the superimposed images thus generated on the stereoscopic display monitor 142.

Figure 9A:
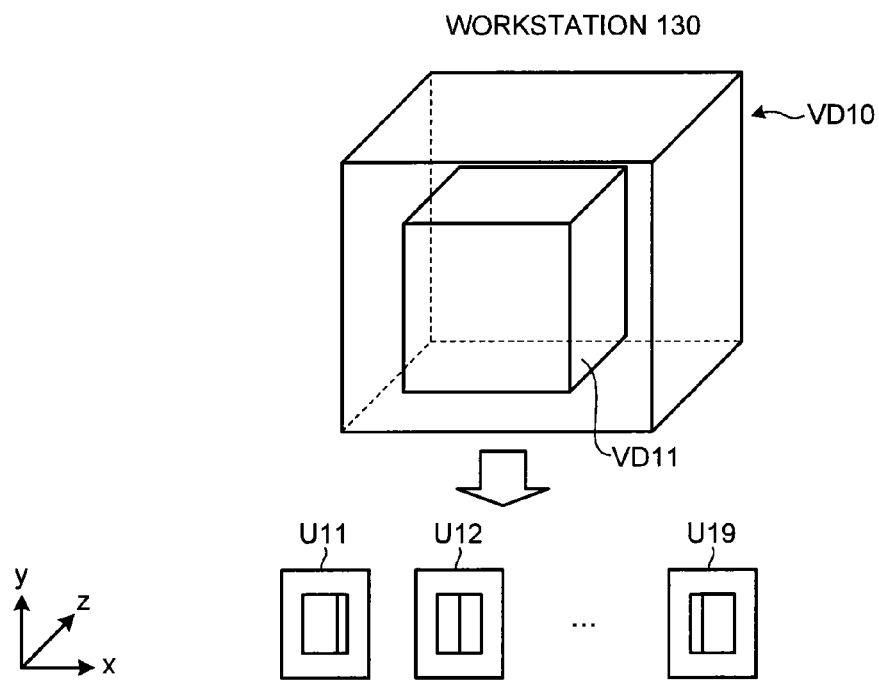
FIG. 9A is a schematic (1) for explaining a process performed by a controller in the first embodiment.
Figure 9B:
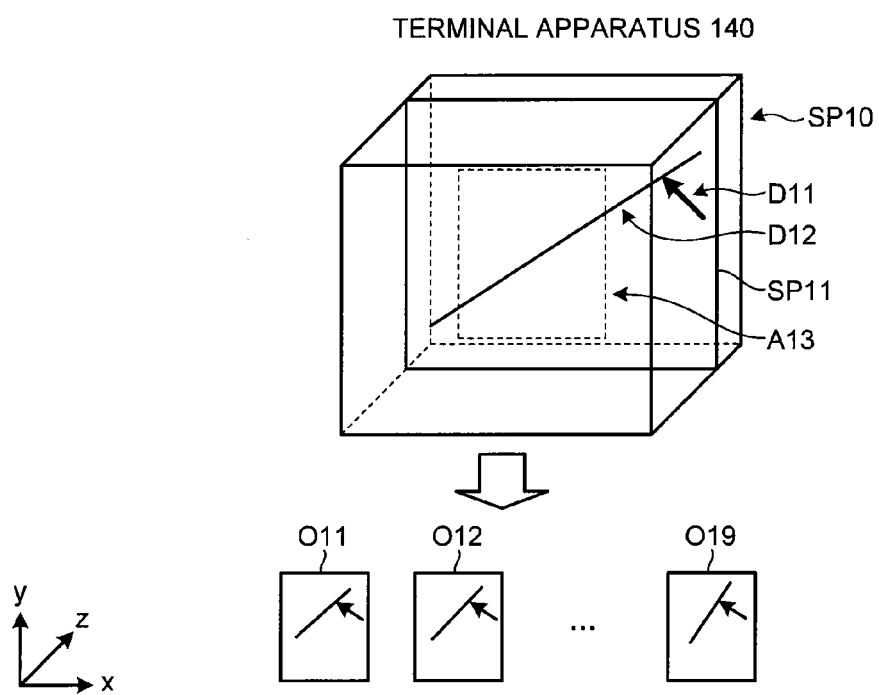
FIG. 9B is a schematic (2) for explaining the process performed by the controller in the first embodiment.
Figure 10:
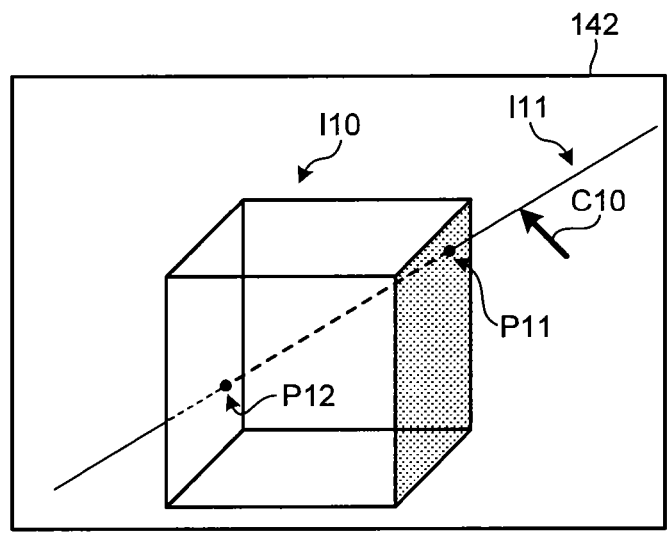
FIG. 10 is a schematic for explaining a process performed by the controller in the first embodiment.

Processes performed by the graphic image generator 1452 and the display controller 1453 will now be explained in detail with reference to FIGS. 9A to 11. FIGS. 9A to 11 are schematics for explaining the process performed by the controller 145 in the first embodiment. To begin with, explained with reference to FIGS. 9A, 9B, and 10 is an example in which a line is displayed as a graphic indicating the cursor position.

In the example illustrated in FIG. 9A, it is assumed that the rendering processor 136 in the workstation 130 generates nine parallax images U11 to U19 by applying a rendering process to the volume data VD10 from a plurality of viewpoint positions. The volume data VD10 includes subject data VD11 that is data representing an organ and the like of a subject. Such subject data VD11 corresponds to the stereoscopic image I10 illustrated as an example in FIG. 7. Data other than the subject data VD11 included in the volume data VD10 indicates things other than the subject, such as the air.

The workstation 130 stores the nine parallax images U11 to U19 thus generated in the image storage apparatus 120, and the terminal apparatus 140 acquires the parallax images U11 to U19 from the image storage apparatus 120. The operation controller 1451 in the terminal apparatus 140 manages the three-dimensional position of the cursor in a cursor virtual space SP10 represented by the same coordinate system as the volume data VD10, in the same manner as the example illustrated in FIG. 9B. The graphic image generator 1452 in the first embodiment acquires the position of the cursor in the cursor virtual space from the operation controller 1451, and plots image data D11 of the cursor to the position thus acquired, and positions image data D12 of a line on a plane SP11 at the same depth-direction position as the cursor within the cursor virtual space SP10.

At this time, the graphic image generator 1452 identifies a region corresponding to the subject data present in the three-dimensional virtual space of the volume data, and identifies the region corresponding to the region thus identified in the cursor virtual space SP10, based on subject position information acquired from the image storage apparatus 120. The graphic image generator 1452 generates the three-dimensional graphic data by plotting the image data D12 of a line connecting a region A13 where the subject data is present and the position pointed by the cursor on the plane SP11 in the cursor virtual space, as illustrated in FIG. 9B as an example.

The shape of the line represented by the image data D12 is not limited to the example illustrated in FIG. 9B. The graphic image generator 1452 may plot any line in any shape on the plane SP11, as long as the line connects the cursor and the subject. For example, the graphic image generator 1452 may plot the image data D12 of a line passing through the position pointed by the cursor and the center or the center of gravity of the region A13 on the plane SP11.

The graphic image generator 1452 then generates graphic images O11 to O19 by performing a volume rendering process to the three-dimensional graphic data plotted with the image data D11 and the image data D12. In performing the rendering process, the graphic image generator 1452 uses the same rendering conditions (e.g., the viewpoint positions, the parallax angle, and the parallax number) as those used when the rendering process is performed to the volume data VD10 by the rendering processor 136. In the example illustrated in FIGS. 9A and 9B, among parallax images U "N (where, N is 11 to 19)" and graphic images O "N (where, N is 11 to 19)", the images having the same N are generated as a result of rendering processes performed under the same rendering conditions. For example, the parallax image U11 and the graphic image O11 are generated as a result of the rendering process performed under the same rendering conditions.

The display controller 1453 generates superimposed images in which, over the parallax images U11 to U19 generated by the rendering processor 136, the respective graphic images O11 to O19 generated by the graphic image generator 1452 and having a matched viewpoint position are superimposed, and displays the superimposed images thus generated on the stereoscopic display monitor 142. To explain using the example illustrated in FIGS. 9A and 9B, the display controller 1453 generates a superimposed image in which the graphic image O11 is superimposed over the parallax image U11. In the same manner, the display controller 1453 generates superimposed images in which, over the parallax image U12 to U19, the respective graphic images O12 to O19 having a matched viewpoint position are superimposed. The display controller 1453 then displays the nine superimposed images thus generated on the stereoscopic display monitor 142. In this manner, the nine superimposed images are displayed on the stereoscopic display monitor 142. As a result, a stereoscopic image enabled to be stereoscopically perceived by an observer is displayed.

Specifically, the stereoscopic display monitor 142 displays the cursor C10 together with the stereoscopic image I10 of the subject, as illustrated in FIG. 10. The stereoscopic display monitor 142 also displays a line image I11 connecting the position pointed by the cursor C10 and the stereoscopic image I10. The line image I11 corresponds to the image data D12 of the line illustrated in FIG. 9B, and is displayed on a plane at the same depth-direction position as the cursor C10 in the stereoscopic image space. Because the line image I11 connects the position pointed by the cursor C10 and the stereoscopic image I10, the observer observing the stereoscopic display monitor 142 illustrated as an example in FIG. 10 can recognize the depth-direction position of the cursor O10. Specifically, by observing an intersection P11 or an intersection P12 between the line image I11 and the stereoscopic image I10, the observer can recognize the depth-direction position of the cursor C10 using the stereoscopic image I10 as a reference.

Described above is an example in which the terminal apparatus 140 displays the line image I11 connecting the cursor C10 and the stereoscopic image I10 indicating the subject. Alternatively, the terminal apparatus 140 may display a line such as a segment or a half line connecting the cursor C10 and the stereoscopic image I10 indicating the subject.

In the example illustrated in FIGS. 9A, 9B and, 10, the graphic image generator 1452 generates three-dimensional graphic data by plotting the image data D12 representing a line on the plane SP11. Alternatively, the graphic image generator 1452 may generate three-dimensional graphic data by plotting image data of a two-dimensional plane having a given size on the plane SP11. In such a case, in the example illustrated in FIG. 9B, the graphic image generator 1452 generates three-dimensional graphic data by plotting image data of a two-dimensional plane on the plane SP11 in the cursor virtual space SP10. For example, the graphic image generator 1452 generates three-dimensional graphic data by plotting image data of a two-dimensional plane including a part of or the entire region A13 where the subject data is present and the position pointed by the cursor on the plane SP11 in the cursor virtual space.

The display controller 1453 generates nine superimposed images in which, over the parallax images U11 to U19 generated by the rendering processor 136, respective graphic images generated by the graphic image generator 1452 and having a matched viewpoint position are superimposed, and displays the nine superimposed images thus generated on the stereoscopic display monitor 142, in the same manner as in the example illustrated in FIGS. 9A and 9B. In this manner, a stereoscopic image is displayed on the stereoscopic display monitor 142 using the nine superimposed images.

Figure 11:
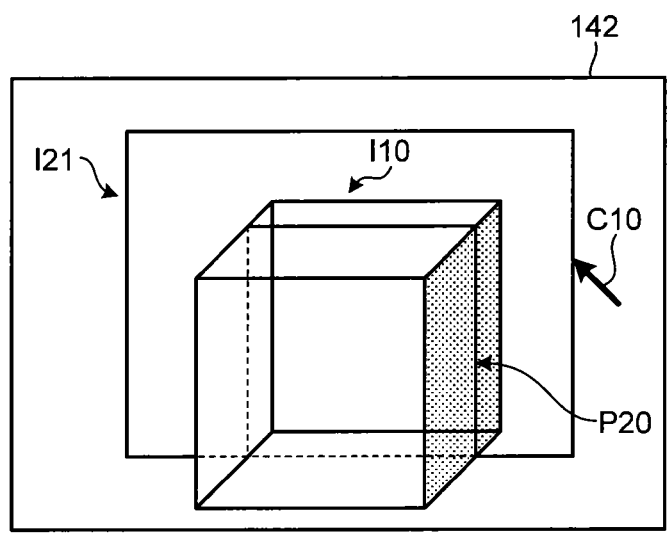
FIG. 11 is a schematic for explaining a process performed by the controller in the first embodiment.

Specifically, the stereoscopic display monitor 142 displays the cursor C10 together with the stereoscopic image I10 representing the subject, as illustrated in FIG. 11. The stereoscopic display monitor 142 also displays a plane image I21 including the position pointed by the cursor C10 and the stereoscopic image I10. The plane image I21 is displayed on a plane at the same depth-direction position as the cursor C10 in the stereoscopic image space, as mentioned earlier. Because the plane image I21 includes the position pointed by the cursor C10 and the stereoscopic image I10, an observer observing the stereoscopic display monitor 142 illustrated as an example in FIG. 11 can recognize the depth-direction position of the cursor C10. Specifically, by observing an intersecting line P20, for example, between the cursor C10 and the stereoscopic image I10, the observer can recognize the depth-direction position of the cursor C10 using the stereoscopic image I10 as a reference.

The graphic image generator 1452 and the display controller 1453 described above perform the process of displaying a graphic image (the line image I11 or the plane image I21) indicating the depth-direction position of the cursor every time the cursor is moved. In other words, in the example illustrated in FIGS. 10 and 11, the line image I11 or the plane image I21 is moved as the cursor is moved.

Figure 12:
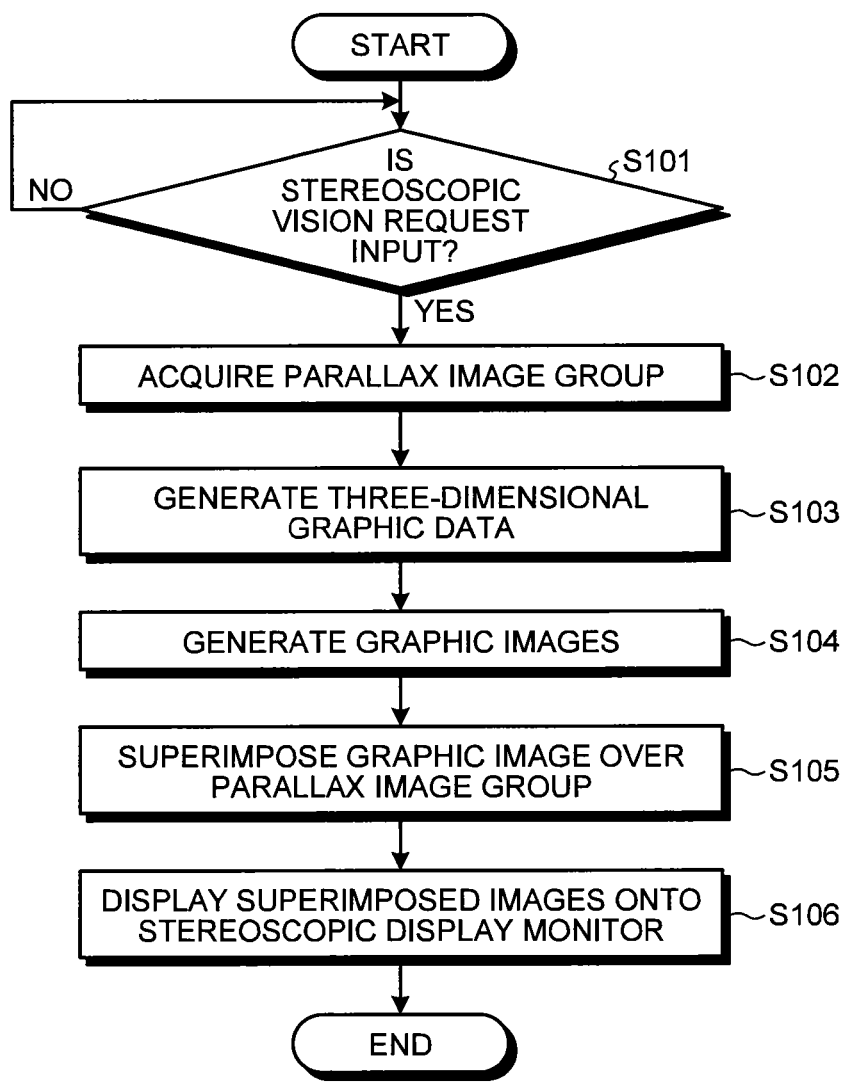
FIG. 12 is a flowchart illustrating an example of a process performed by the terminal apparatus in the first embodiment.

A process performed by the terminal apparatus 140 in the first embodiment will now be explained with reference to FIG. 12. FIG. 12 is a flowchart illustrating an example of the process performed by the terminal apparatus 140 in the first embodiment.

As illustrated in FIG. 12, the controller 145 in the terminal apparatus 140 determines if a stereoscopic vision request is input by an observer using the input unit 141 (Step S101). If no stereoscopic vision request is input (No at Step S101), the terminal apparatus 140 waits until a stereoscopic vision request is input.

By contrast, if a stereoscopic vision request is input (Yes at Step S101), the controller 145 transmits the stereoscopic vision request to the image storage apparatus 120, and acquires a parallax image group from the image storage apparatus 120 (Step S102).

The graphic image generator 1452 in the controller 145 then generates the three-dimensional graphic data by plotting the image data of the cursor and the image data such as a line or a two-dimensional plane representing the position of the cursor in the cursor virtual space (Step S103). The graphic image generator 1452 then generates a plurality of graphic images by applying a volume rendering process to the three-dimensional graphic data (Step S104).

The display controller 1453 in the controller 145 then generates a plurality of superimposed images by superimposing, over the parallax image group acquired from the image storage apparatus 120, a plurality of respective graphic images generated by the graphic image generator 1452 and having a matched viewpoint position (Step S105). The display controller 1453 then displays the superimposed images thus generated on the stereoscopic display monitor 142 (Step S106).

As described above, according to the first embodiment, by displaying a line or a two-dimensional plane as a graphic indicating the cursor position, an observer is enabled to recognize the position of a cursor displayed along with a stereoscopic image.

Explained in the first embodiment is an example in which the graphic image generator 1452 generates the three-dimensional graphic data by plotting image data of a line connecting the region A13 in which the subject data is present and the position pointed by the cursor in the cursor virtual space, and the display controller 1453 displays the image of the line connecting the cursor and the subject, as explained with reference to FIGS. 9A, 9B, and 10. Alternatively, the graphic image generator 1452 may plot image data of a line connecting the position pointed by the cursor and the center or the center of gravity of the cursor virtual space in the cursor virtual space, without identifying the region A13 where the subject data is present.

Specifically, generally speaking, the subject data VD11 is often positioned at the center of the volume data VD10 in the example illustrated in FIG. 9A. Therefore, in the example illustrated in FIG. 9B, the line connecting the position pointed by the cursor and the center or the center of gravity of the cursor virtual space generally passes through the region A13 corresponding to the position of the subject data VD11. Thus, the graphic image generator 1452 may also plot image data of a line connecting the position pointed by the cursor and the center or the center of gravity of the plane SP11 in the cursor virtual space. When such a process is performed, because the graphic image generator 1452 is not required to perform the process of identifying the region A13 where the subject data is present, the load in generating graphic images can be reduced.

For the same reason, in the example explained with reference to FIG. 11, the graphic image generator 1452 may generate three-dimensional graphic data by plotting the image data of a two-dimensional plane including the position pointed by the cursor and the center or the center of gravity of the plane SP11 in the cursor virtual space. In such a case as well, because the graphic image generator 1452 is not required to perform the process of identifying the region A13 where the subject data is present, the load in generating graphic images can be reduced.

Furthermore, in the first embodiment, the terminal apparatus 140 may display the line image I11 or the plane image I21 illustrated as an example in FIGS. 9A, 9B, and 10, in response to a particular operation.

Furthermore, in the first embodiment, the terminal apparatus 140 may receive information related to the shape of the line image I11 illustrated as an example in FIG. 10, or the shape of the plane image I21 illustrated as an example in FIG. 11 from an observer. For example, the terminal apparatus 140 may receive an angle formed between the line image I11 and the lateral direction (x-axis direction), opacity of the line image I11, or a request for displaying the line image I11 as a dotted line, a curve or the like, instead of a line, via the input unit 141. The terminal apparatus 140 may also receive the size of the plane image I21, opacity of the plane image I21, or a request for displaying the plane image I21 as a polygon, a circle, or an ellipse, instead of a rectangle, for example. In such a case, the graphic image generator 1452 determines the shape of the line image I11 or the plane image I21 based on the shape-related information received via the input unit 141.

Furthermore, in the first embodiment, the terminal apparatus 140 may also display an image of a plane perpendicularly intersecting with the plane image I21, in addition to the plane image I21 that is in parallel with an xy plane, as illustrated in the example in FIG. 11. In other words, the terminal apparatus 140 may display a plane image that is in parallel with the xz plane and a plane image that is in parallel with the yz plane, in addition to the plane image that is in parallel with the xy plane.

Furthermore, in the first embodiment, the operation controller 1451 may limit the movable range of the cursor to a range where the line image I11 is displayed in response to a given operation performed using the input unit 141. For example, in the example illustrated in FIG. 10, in response to a given operation performed while exemplary various images illustrated in FIG. 10 are displayed on the stereoscopic display monitor 142, the operation controller 1451 may fix the position where the line image I11 is displayed, and limit the movable range of the cursor C10 to positions along the line image I11. Alternatively, the operation controller 1451 may fix the position where the line image I11 is displayed, and limit the movable range of the cursor C10 to the positions along the line image I11 within the stereoscopic image I10. Furthermore, in response to a given operation, the operation controller 1451 may fix the position where the line image I11 is displayed, and move the cursor C10 to the intersection P11 or the intersection P12 between the stereoscopic image I10 and the line image I11.

Similarly, in the example illustrated in FIG. 11, in response to a given operation performed while exemplary various images illustrated in FIG. 11 are displayed on the stereoscopic display monitor 142, the operation controller 1451 may fix the position where the plane image I21 is displayed, and limit the movable range of the cursor C10 to positions on the plane image I21. Alternatively, the operation controller 1451 may fix the position where the plane image I21 is displayed, and limit the movable range of the cursor C10 to positions on the plane image I21 within the stereoscopic image I10. Alternatively, in response to a given operation, the operation controller 1451 may fix the position where the plane image I21 is displayed, and move the cursor C10 to the intersecting line P20 between the stereoscopic image I10 and the plane image I21, for example.

In this manner, an observer is enabled to move the cursor while the depth direction is fixed. For example, in the example illustrated in FIG. 10, when the observer wants to move the cursor C10 to the intersection P11, the observer can fix the depth-direction position of the cursor C10 simply by performing the given operation. Therefore, the observer can move the cursor C10 to the intersection P11 easily.

Furthermore, when a plane image perpendicularly intersecting with the plane image I21 (a plane image in parallel with the xz plane or a plane image in parallel with the yz plane) is displayed, the operation controller 1451 may also fix the position where the plane image in parallel with the xz plane or the plane image in parallel with the yz plane is displayed, and limit the movable range of the cursor C10 to the positions on the plane image I21, positions on the plane image in parallel with the xz plane, or positions on the plane image in parallel with the yz plane.

Because the operation controller 1451 controls the movement of the cursor in the cursor virtual space, the operation controller 1451 can control the movement of the cursor in the manner explained above based on the position of the image data D12 (corresponding to the line image I11) of a line and the like placed in the cursor virtual space, for example.

Second Embodiment

Explained in the first embodiment is an example in which an observer is enabled to recognize the position of the cursor in the depth direction by displaying a given graphic (a line or a plane) on a plane that is at the same depth-direction position as the cursor. Explained below is another embodiment in which a cursor and a graphic indicating a depth-direction position are displayed. To begin with, explained in a second embodiment is an example in which a contour line (isogram) corresponding to a depth-direction component is displayed on the surface of an organ and the like of a subject in the stereoscopic image displayed on the stereoscopic display monitor 142.

A terminal apparatus 240 in the second embodiment will now be explained. The terminal apparatus 240 corresponds to the terminal apparatus 140 illustrated in FIG. 1. Because the configuration of the terminal apparatus 240 in the second embodiment is the same as the exemplary configuration of the terminal apparatus 140 illustrated in FIG. 8, a drawing of the terminal apparatus 240 is omitted. The terminal apparatus 240 in the second embodiment, however, performs different processes from those performed by the graphic image generator 1452 and the display controller 1453 included in the terminal apparatus 140. Therefore, assuming that the terminal apparatus 240 includes a graphic image generator 2452 and a display controller 2453, instead of the graphic image generator 1452 and the display controller 1453 included in the terminal apparatus 140, these processing units will be explained.

The graphic image generator 2452 in the second embodiment generates a graphic image including an image of a contour line corresponding to a component of the depth direction on the surface of a subject. In other words, the graphic image generator 2452 uses a contour line of a depth-direction component as a graphic indicating a cursor position.

Specifically, the graphic image generator 2452 identifies the region where the subject data is present in the three-dimensional virtual space plotted with the volume data from which a parallax image group is generated, based on subject position information acquired from the image storage apparatus 120, and identifies the region of the cursor virtual space corresponding to the region thus identified. In other words, although the cursor virtual space has no subject data, the graphic image generator 2452 identifies the region corresponding to the region where the subject data is present in the cursor virtual space using the subject position information. The graphic image generator 2452 then generates three-dimensional graphic data by plotting image data of contour lines in the depth direction (z-direction) on the surface of the region corresponding to the subject data in the cursor virtual space. For example, the graphic image generator 2452 generates three-dimensional graphic data representing contour lines by plotting a line connecting a group of points located at the same depth-direction position on the surface of the region corresponding to the subject data at a given interval (e.g., an interval of 1 centimeter in the real scale of the subject) in the depth direction in the cursor virtual space. The graphic image generator 2452 then generates a plurality of graphic images by performing a volume rendering process to the three-dimensional graphic data thus generated, from the same viewpoint positions as those used in generating the parallax image group. The contour line may be a line, a dotted line, a translucent line, or a translucent dotted line.

The display controller 2453 in the second embodiment then generates nine superimposed images in which, over the parallax image group generated by the rendering processor 136, the respective graphic images generated by the graphic image generator 2452 and having a matched viewpoint position are superimposed, and displays the nine superimposed images thus generated on the stereoscopic display monitor 142. In this manner, a stereoscopic image is displayed on the stereoscopic display monitor 142 using the nine superimposed images.

FIG. 13 illustrates an example of a stereoscopic image displayed on the stereoscopic display monitor 142 in the second embodiment. As illustrated in FIG. 13, the stereoscopic display monitor 142 displays the cursor C10 together with the stereoscopic image I10 representing a subject. The stereoscopic display monitor 142 also displays contour line images I31 to I34 on the surface of the stereoscopic image I10 of the subject. Because these contour line images I31 to I34 correspond to the image data of contour lines plotted by the graphic image generator 2452, the contour line images I31 to I34 are displayed at the given interval in the stereoscopic image space along the depth direction, and each of these contour line images I31 to I34 is displayed on the same plane having the same depth-direction component in the stereoscopic image space. Therefore, an observer observing the stereoscopic display monitor 142 illustrated as an example in FIG. 13 can recognize the depth-direction position of the cursor C10 by moving the cursor C10 closer to the stereoscopic image I10. Specifically, in the example illustrated in FIG. 13, the observer can recognize that the depth-direction position of the cursor C10 is near the contour line image I32.

As described above, according to the second embodiment, by displaying contour lines on the surface of a subject as a graphic indicating a cursor position, an observer is enabled to recognize the position of a cursor displayed with a stereoscopic image.

In the second embodiment, the terminal apparatus 240 may receive information related to the interval of the contour lines. For example, the terminal apparatus 240 may receive the interval in the real scale of a subject (e.g., 1 centimeter) via the input unit 141, as an interval for displaying the contour lines. In such a case, the graphic image generator 2452 determines the number of contour line image data to be positioned in the cursor virtual space based on the information related to the interval of the contour lines received via the input unit 141.

Third Embodiment

Explained in a third embodiment is an example in which the color of the cursor is varied depending on the depth-direction position of the cursor displayed on the stereoscopic display monitor 142.

A terminal apparatus 340 in the third embodiment will now be explained. The terminal apparatus 340 corresponds to the terminal apparatus 140 illustrated in FIG. 1. Because the configuration of the terminal apparatus 340 in the third embodiment is the same as the exemplary configuration of the terminal apparatus 140 illustrated in FIG. 8, a drawing of the terminal apparatus 340 is omitted. The terminal apparatus 340 in the third embodiment, however, performs different processes from those performed by the graphic image generator 1452 and the display controller 1453 included in the terminal apparatus 140. Therefore, assuming that the terminal apparatus 340 includes a graphic image generator 3452 and a display controller 3453, instead of the graphic image generator 1452 and the display controller 1453 included in the terminal apparatus 140, these processing units will be explained.

The graphic image generator 3452 in the third embodiment generates an image including a cursor that is colored differently depending on the depth-direction position. At this time, the graphic image generator 3452 also generates an image of a graphic indicating the distribution of colors applied to the cursor and having a shape extending in the depth direction, in addition to the cursor image.

Specifically, the graphic image generator 3452 generates three-dimensional graphic data by plotting image data of a three-dimensional graphic assigned with colors varying corresponding to the depth-direction position of the graphic in the cursor virtual space, and image data of a cursor in a given color in the cursor virtual space. For example, the graphic image generator 3452 plots image data of a three-dimensional graphic assigned with different colors a given interval in the real scale of the subject (e.g., an interval of 1 centimeter) in the cursor virtual space. The graphic image generator 3452 generates the three-dimensional graphic data by identifying a color corresponding to the position of the cursor from the colors assigned to the three-dimensional graphic, and plotting image data of a cursor applied with the color thus identified in the cursor virtual space. The graphic image generator 3452 then generates a plurality of graphic images by applying a rendering process to the three-dimensional graphic data thus generated from the viewpoint positions used when the parallax image group is generated.

The display controller 3453 in the third embodiment generates nine superimposed images in which, over the parallax image group generated by the rendering processor 136, the respective graphic images generated by the graphic image generator 3452 and having a matched viewpoint position are superimposed, and displays the nine superimposed images thus generated on the stereoscopic display monitor 142. In this manner, a stereoscopic image is displayed on the stereoscopic display monitor 142 using the nine superimposed images.

Figure 14A:
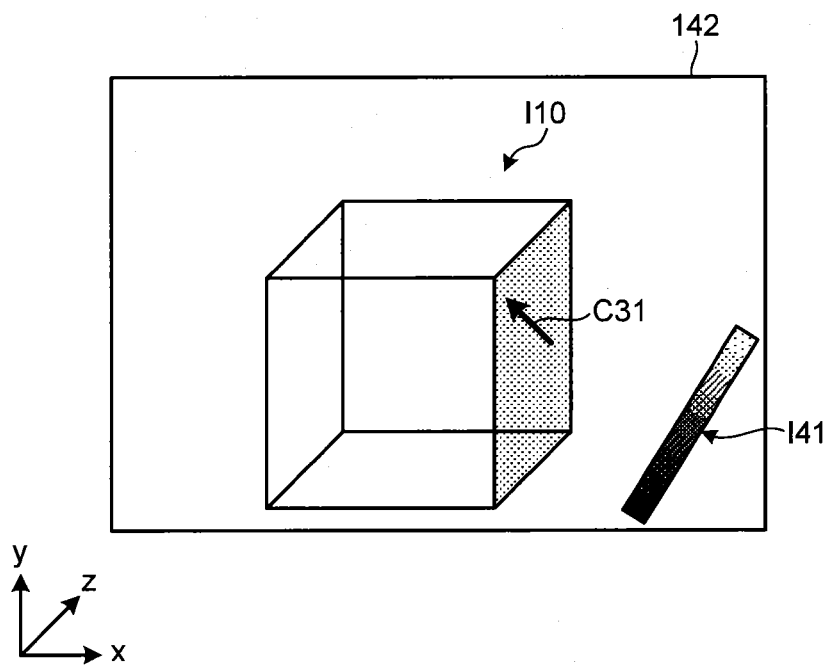
FIG. 14A is a schematic (1) illustrating an example of a stereoscopic image displayed on a stereoscopic display monitor in a third embodiment.
Figure 14B:
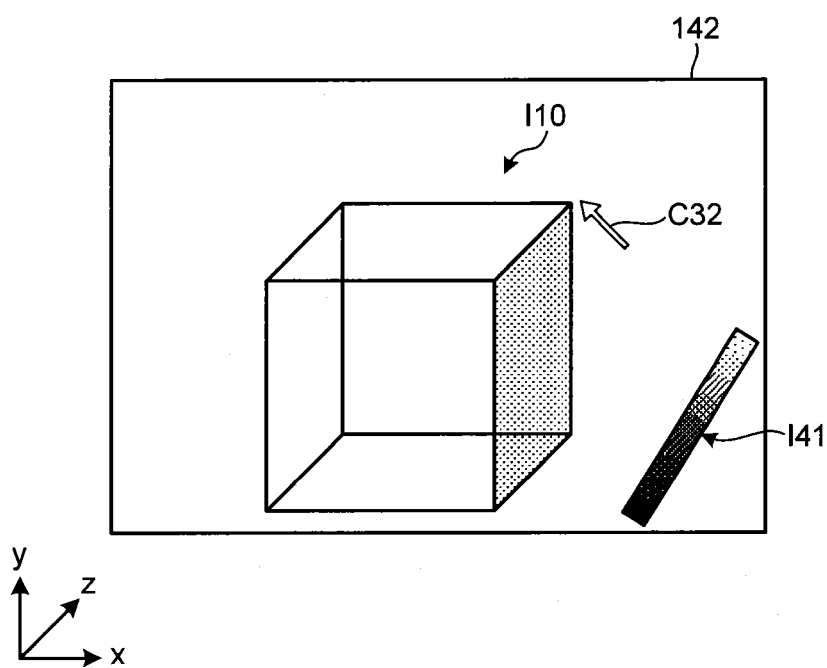
FIG. 14B is a schematic (2) illustrating an example of the stereoscopic image displayed on the stereoscopic display monitor in the third embodiment.

FIGS. 14A and 14B illustrate examples of a stereoscopic image displayed on the stereoscopic display monitor 142 in the third embodiment. In FIGS. 14A and 14B, the cursor is at different positions. In the example illustrated in FIG. 14A, the stereoscopic display monitor 142 displays the stereoscopic image I10 of the subject, a three-dimensional graphic I41, and a cursor C31 in a given color. In the example illustrated in FIG. 14B, the stereoscopic image I10, the three-dimensional graphic I41, and a cursor C32 are displayed. The three-dimensional graphic I41 illustrated in FIGS. 14A and 14B is a graphic displayed three-dimensionally in the stereoscopic image space, and is assigned with colors varying corresponding to the depth-direction positions in the stereoscopic image space. In the examples illustrated in FIGS. 14A and 14B, the three-dimensional graphic I41 has a color nearer to black at a position nearer to the observer, and has a color nearer to white at a position further away from the observer.

The cursor C31 illustrated in FIG. 14A is displayed at a position near the observer in the stereoscopic image space, and is colored black. The cursor C32 illustrated in FIG. 14B is displayed at a position further away from the observer in the stereoscopic image space, and is colored white. The cursors C31 and C32 are assigned with a color corresponding to the depth-direction position of the cursor, among the colors provided to the three-dimensional graphic I41. Therefore, an observer observing the stereoscopic display monitor 142 illustrated as an example in FIG. 14A and FIG. 14B can recognize the position of the cursor in the depth direction based on the color applied to the cursor. Specifically, by looking at the colors provided to the three-dimensional graphic I41 and the color provided to the cursor, the observer can recognize the position of the cursor in the depth direction.

As described above, according to the third embodiment, because the color in which the cursor is displayed is varied corresponding to the depth direction, an observer is enabled to recognize the position of the cursor displayed with a stereoscopic image.

In the third embodiment, the terminal apparatus 340 may not display the three-dimensional graphic I41 that is used as a legend of the cursor color. For example, when the colors applied to the cursor corresponding to the depth-direction position are fixed by system specifications, and such colors are known to the observers, the three-dimensional graphic I41 does not need to be displayed on the terminal apparatus 340.

Furthermore, in the third embodiment, the terminal apparatus 340 may also assign different colors to the subject depending on the depth-direction position. In this manner, by moving the cursor closer to the stereoscopic image of the subject, an observer can recognize the position of the cursor in the depth direction.

Fourth Embodiment

Explained in a fourth embodiment is an example in which a region of the subject is projected on the cursor depending on the depth-direction position of the cursor displayed on the stereoscopic display monitor 142.

To begin with, a terminal apparatus 440 in the fourth embodiment will be explained with reference to FIG. 15. FIG. 15 is a schematic for explaining an exemplary configuration of the terminal apparatus 440 in the fourth embodiment. In the explanations below, elements having already explained are assigned with the same reference numerals, and detailed explanations thereof are omitted herein. The terminal apparatus 440 illustrated in FIG. 15 corresponds to the terminal apparatus 140 illustrated in FIG. 1. The terminal apparatus 440 includes a controller 445, as illustrated as an example in FIG. 15. The controller 445 includes a light source setting module 4454, a graphic image generator 4452, and a display controller 4453.

The light source setting module 4454 sets a virtual light source that is a virtual light source in the cursor virtual space. Specifically, the light source setting module 4454 determines the position and a type of the virtual light source to be set in the three-dimensional cursor virtual space when the graphic image generator 4452, which is to be described later, generates graphic images. Examples of types of the virtual light source include a light source outputting parallel light rays from the infinity, and a light source emitting radial light rays from the position of the virtual light source.

The graphic image generator 4452 generates an image of a cursor on which a region in a subject (hereinafter sometimes referred to as a "target region") is projected. Specifically, the graphic image generator 4452 generates an image of the cursor on which a shadow of a target region is cast, by using the cursor as a projection surface, and projecting a target region on the cursor that is a projection surface based on the virtual light source set by the light source setting module 4454.

To explain more specifically, the graphic image generator 4452 identifies the region where the subject data is present within the three-dimensional virtual space plotted with the volume data from which the parallax image group is generated, and identifies the region corresponding to the region thus identified in the cursor virtual space, based on the subject position information acquired from the image storage apparatus 120. If the subject data is present between the virtual light source set by the light source setting module 4454 and the cursor in the cursor virtual space, the graphic image generator 4452 generates three-dimensional graphic data by plotting image data of the cursor on which a shadow of the subject data is cast in the cursor virtual space. At this time, under an assumption that the light is coming from the virtual light source, the graphic image generator 4452 assigns an image of the target region projected by the light to the cursor as a shadow. The graphic image generator 4452 then generates a plurality of graphic images by performing a rendering process to the three-dimensional graphic data thus generated, using the same viewpoint positions as those used in generating the parallax image group.

The graphic image generator 4452 may change lightness of the shadow cast on the cursor depending on the distance between the cursor and the target region. For example, the graphic image generator 4452 casts a shadow in darker black on the cursor when the distance between the cursor and the target region is nearer, and casts a shadow in lighter black to the cursor when the distance between the cursor and the target region is further.

The display controller 4453 then generates nine superimposed images in which, over the parallax image group generated by the rendering processor 136, a plurality of respective graphic images generated by the graphic image generator 4452 and having a matched viewpoint position are superimposed, and displays the nine superimposed images thus generated on the stereoscopic display monitor 142. In this manner, a stereoscopic image is displayed on the stereoscopic display monitor 142 using the nine superimposed images.

Figure 16:
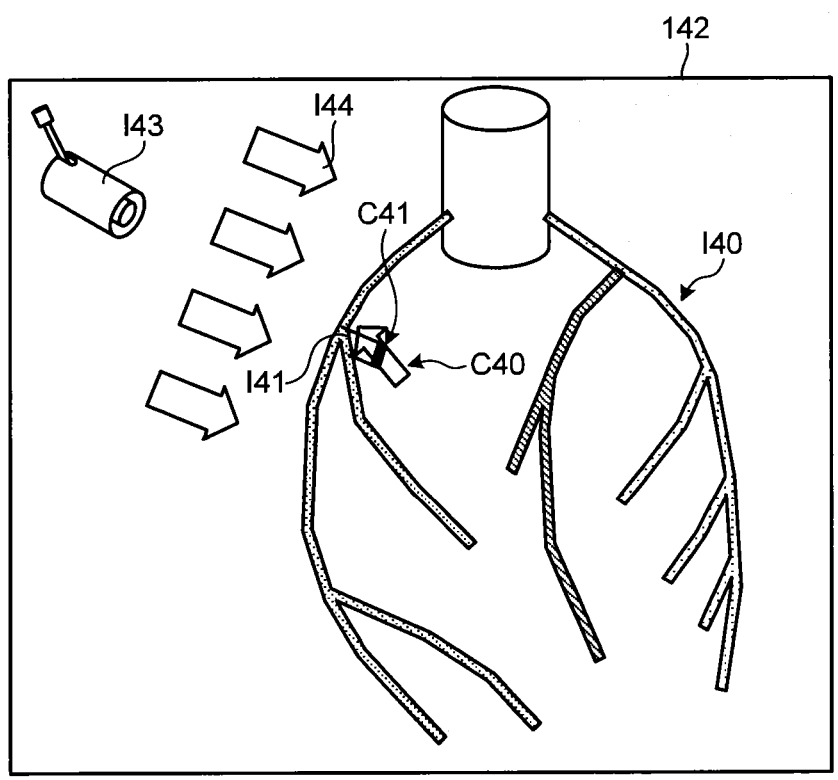
FIG. 16 is a schematic illustrating an example of a stereoscopic image displayed on the stereoscopic display monitor in the fourth embodiment.

FIG. 16 illustrates an example of a stereoscopic image displayed on the stereoscopic display monitor 142 in the fourth embodiment. As illustrated in FIG. 16, the stereoscopic display monitor 142 displays a stereoscopic image I40 representing a region in a subject, and a cursor C40. A target region I41 of the stereoscopic image I40 is projected on the cursor C40. Specifically, a shadow image C41 of the target region I41 is cast on the cursor C40. Therefore, an observer observing the stereoscopic display monitor 142 illustrated as an example in FIG. 16 can recognize the depth-direction position of the cursor C40 based on the shadow image cast on the cursor C40. Specifically, the observer can understand that the cursor C40 is located at a position further away from the region I41 with respect to the observer.

As described above, according to the fourth embodiment, by displaying a shadow of the subject on the cursor on which the target region is projected, an observer is enabled to recognize the position of the cursor displayed with a stereoscopic image.

In the fourth embodiment, the terminal apparatus 440 may also display an image of the virtual light source or a schematic image of the light output from the virtual light source. To explain using the example illustrated in FIG. 16, the terminal apparatus 440 may display an image I43 of the virtual light source or a schematic image I44 of the light output from the virtual light source. In this manner, because the observer can understand the position of the virtual light source or the direction of the light output from the virtual light source, the observer can easily recognize the position of the cursor.

Furthermore, in the fourth embodiment, the terminal apparatus 440 may also receive information related to the position of the virtual light source from the observer. For example, the terminal apparatus 440 may receive coordinates of the position where the virtual light source is positioned via the input unit 141. In such a case, the light source setting module 4454 positions the virtual light source in the cursor virtual space based on the information related to the virtual light source received via the input unit 141.

Furthermore, in the fourth embodiment, the light source setting module 4454 may change the position of the virtual light source dynamically based on the position of the cursor. Specifically, the light source setting module 4454 may change the position of the virtual light source dynamically so that a region in the subject comes between the cursor and the virtual light source. In other words, the light source setting module 4454 may move the virtual light source to a position along a line connecting the cursor and the region in the subject. In this manner, the terminal apparatus 440 can increase the probability at which a region in the subject is projected on the cursor, and, as a result, the observer is enabled to recognize the position of the cursor.

Fifth Embodiment

Explained in a fifth embodiment is an example in which lightness or the like is varied in radial directions, centering on the position of the cursor displayed on the stereoscopic display monitor 142.

A terminal apparatus 540 in the fifth embodiment will now be explained. The terminal apparatus 540 corresponds to the terminal apparatus 140 illustrated in FIG. 1. Because the configuration of the terminal apparatus 540 in the fifth embodiment is the same as the exemplary configuration of the terminal apparatus 140 illustrated in FIG. 8, a drawing of the terminal apparatus 540 is omitted. The terminal apparatus 540 in the fifth embodiment, however, performs different processes from those performed by the graphic image generator 1452 and the display controller 1453 included in the terminal apparatus 140. Therefore, assuming that the terminal apparatus 540 includes a graphic image generator 5452 and a display controller 5453, instead of the graphic image generator 1452 and the display controller 1453 included in the terminal apparatus 140, these processing units will be explained.

The graphic image generator 5452 in the fifth embodiment generates an image of a cursor, and a graphic image having lightness varied in radial directions, centering on the position of the cursor. Specifically, the graphic image generator 5452 generates the three-dimensional graphic data by plotting image data of a cursor to the position of the cursor in the cursor virtual space. The graphic image generator 5452 then generates a plurality of graphic images by performing a volume rendering process to the three-dimensional graphic data thus generated, from the same viewpoint positions used in generating the parallax image group. At this time, the graphic image generator 5452 performs the volume rendering process by changing the lightness or the like in radial directions, centering on the position of the cursor. For example, the graphic image generator 5452 applies a volume rendering process by reducing the lightness for positions nearer to the cursor, and increasing the lightness for positions further away from the cursor. Alternatively, the graphic image generator 5452 applies a volume rendering process by increasing the lightness for positions nearer to the cursor, and reducing the lightness for positions further away from the cursor, in a manner opposite to the example explained above, for example. The color in which the lightness is varied by the graphic image generator 5452 may be any color.

Furthermore, the display controller 5453 in the fifth embodiment generates nine superimposed images in which, over the parallax image group generated by the rendering processor 136, a plurality of respective graphic images generated by the graphic image generator 5452 and having a matched viewpoint position are superimposed, and displays the nine superimposed images thus generated on the stereoscopic display monitor 142. In this manner, a stereoscopic image is displayed on the stereoscopic display monitor 142 using the nine superimposed images.

Figure 17A:
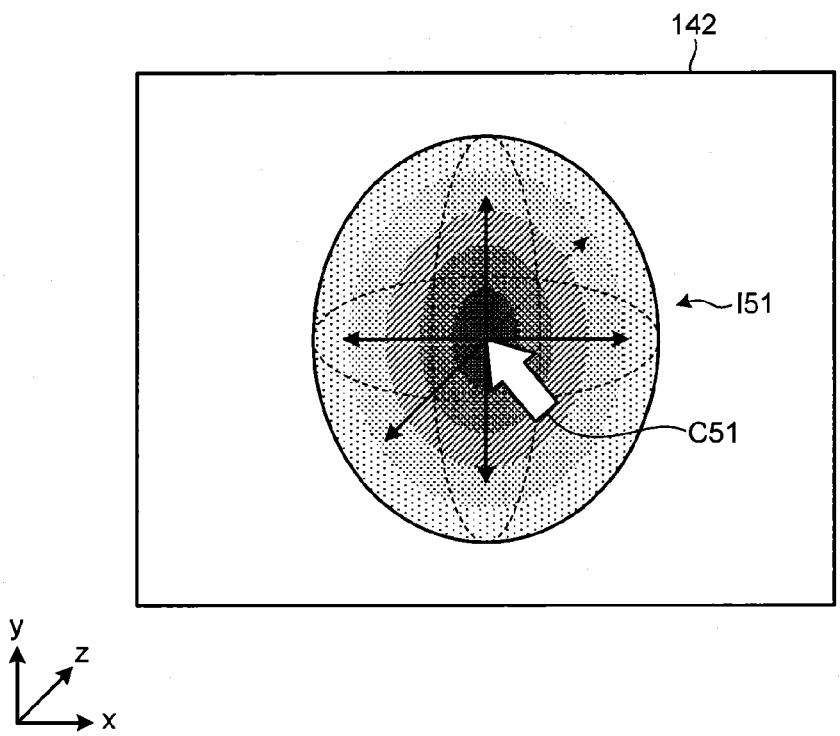
FIG. 17A is a schematic (1) illustrating an example of a stereoscopic image displayed on a stereoscopic display monitor in a fifth embodiment.
Figure 17B:
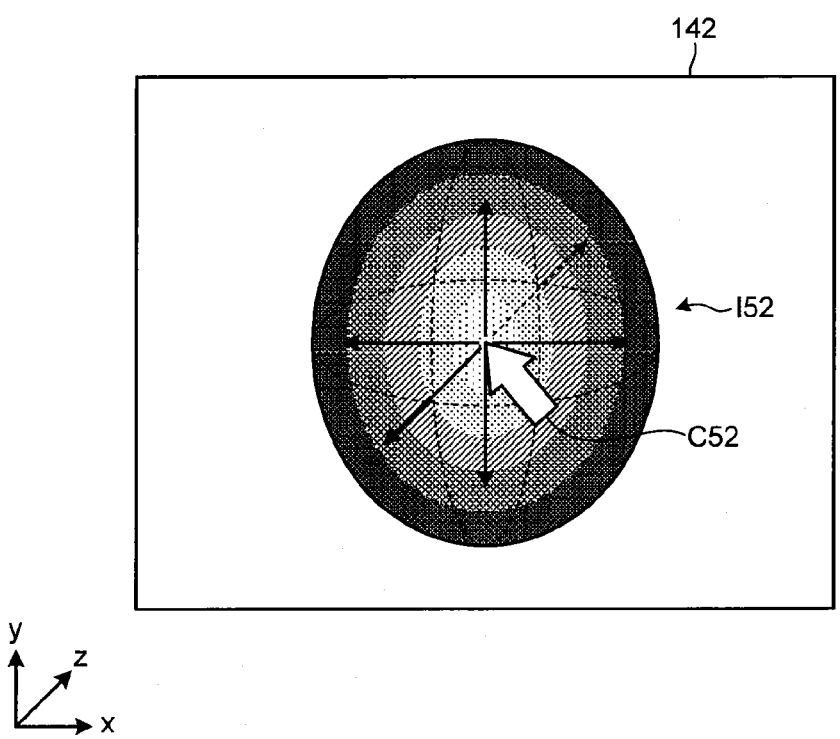
FIG. 17B is a schematic (2) illustrating an example of the stereoscopic image displayed on the stereoscopic display monitor in the fifth embodiment.

FIGS. 17A and 17B illustrate examples of a stereoscopic image displayed on the stereoscopic display monitor 142 in the fifth embodiment. In the example illustrated in FIG. 17A, a stereoscopic image I51 representing a subject, and a cursor C51 are displayed on the stereoscopic display monitor 142. The stereoscopic image I51 is displayed as having lower lightness to higher lightness, varying in the radial directions, centering on the position pointed by the cursor C51. In other words, in the stereoscopic image I51, a position pointed by the cursor C51 is displayed dark, and positions away from the position pointed by the cursor C51 are displayed lighter.

As an alternative, in the example illustrated in FIG. 17B, a stereoscopic image I52 representing a subject, and a cursor C52 are displayed on the stereoscopic display monitor 142. The stereoscopic image I52 is displayed as having higher lightness to lower lightness, varying in radial directions, centering on the position pointed by the cursor C52. In other words, in the stereoscopic image I52, the position pointed by the cursor C52 is displayed light, and positions away from the position pointed by the cursor C52 are displayed darker.

An observer observing the stereoscopic display monitor 142 illustrated as an example in FIGS. 17A and 17B can recognize the position of the cursor in the depth direction based on the lightness near the position pointed by the cursor. For example, because the position pointed by the cursor is displayed dark in the example illustrated in FIG. 17A and the position pointed by the cursor is displayed light in the example illustrated in FIG. 17B, an observer can recognize the position of the cursor in the depth direction using the lightness.

As described above, according to the fifth embodiment, by displaying the stereoscopic image with varying lightness, centering on the position pointed by the cursor, an observer is enabled to recognize the position of the cursor displayed with a stereoscopic image.

In the fifth embodiment, the terminal apparatus 540 may also display an x-axis, a y-axis, and a z-axis of three-dimensional coordinates having a point of origin at the position pointed by the cursor, in the manner illustrated in the example of FIGS. 17A and 17B.

Furthermore, in the fifth embodiment, the color in which the terminal apparatus 540 varies the lightness may be any color. Furthermore, such a color may be in singularity, or two or more colors. For example, in the example illustrated in FIG. 17A, the terminal apparatus 540 may display the color in a manner varying from black to white, or from red to blue in radial directions, centering on the position pointed by the cursor C51.

Furthermore, in the fifth embodiment, the terminal apparatus 540 may display a stereoscopic image having varying contrast along radial directions, centering on the position pointed by the cursor.

Furthermore, in the fifth embodiment, the terminal apparatus 540 may perform a control of displaying the stereoscopic image in a manner lightness or contrast varied only one time in response to a given operation. Specifically, when a pointing device and the like is clicked, the graphic image generator 5452 and the display controller 5453 included in the terminal apparatus 540 display the stereoscopic image in varying lightness or contrast, by performing the process explained above. The terminal apparatus 540 may then recover the display mode without changing the lightness or the like, after a given time elapses, by displaying the parallax image group acquired from the image storage apparatus 120.

Furthermore, the terminal apparatus 540 may switch between a display mode for changing the lightness or the like and a display mode without changing lightness or the like at a given interval in response to a given operation. Furthermore, the terminal apparatus 540 may make the interval in which these two display modes are switched variable. Furthermore, the terminal apparatus 540 may be fixed to one of these display modes in response to a given operation while both display modes are switched, and restart the operation of switching these two display modes in response to a given operation performed while the terminal apparatus 540 is fixed to one of the display modes.

Furthermore, in the fifth embodiment, the terminal apparatus 540 may increase the contrast of a given (e.g., spherical, ellipsoidal, or cubic) area centering on the position pointed by the cursor, and reduces the contrast of the area other than the given area. Furthermore, the terminal apparatus 540 may allocate a color only to such a given area, and no color to the area other than the given area. Furthermore, the terminal apparatus 540 may display the lightness or the contrast varied within such a given area, in radial directions, centering on the position of the cursor.

Explained now specifically is a process of increasing the contrast only in or applying a color only to a given area. When such a process is to be performed, the graphic image generator 5452 generates the three-dimensional graphic data by not only plotting image data of a cursor to the position of the cursor in the cursor virtual space, but also plotting a graphic, such as a sphere, centering on the position of the cursor in the cursor virtual space. The graphic image generator 5452 then generates a plurality of graphic images by applying a volume rendering process to the three-dimensional graphic data from the same viewpoint positions used in generating the parallax image group. At this time, the volume rendering process is performed by changing the lightness within the graphic such as a sphere included in the three-dimensional graphic data, depending on the distance from the cursor.

Explained now with reference to FIG. 18 is an example for displaying a stereoscopic image in which the contrast is increased only within the given area. In the example illustrated in FIG. 18, a stereoscopic image I53 representing a subject, a cursor C53, and a sphere image I54 centering on the position pointed by the cursor C53 are displayed on the stereoscopic display monitor 142. The area corresponding to the sphere image I54 in the stereoscopic image I53 is displayed in higher contrast, and the area other than the sphere image I54 in the stereoscopic image I53 is displayed in lower contrast. Alternatively, the terminal apparatus 540 may display the area corresponding to the sphere image I54 in a given color, and the area other than the sphere image I54 without any color, in the example illustrated in FIG. 18. For example, the terminal apparatus 540 displays the area other than the sphere image I54 transparent. In this manner, an observer can recognize the position of the cursor in the depth direction based on the contrast or the lightness of the area near the position pointed by the cursor.

The three-dimensional area, such as the sphere image I54, displayed at different contrast or in a different color does not have to be created centering on the position pointed by the cursor. For example, the graphic image generator 5452 may also generate the three-dimensional graphic data by plotting a graphic, such as a sphere, including the position of the cursor in the cursor virtual space. Furthermore, the terminal apparatus 540 may receive information related to the size or the position of the three-dimensional area, such as the sphere image I54, displayed at a different contrast or in a different color from an observer via the input unit 141. In such a case, the terminal apparatus 540 determines the size or the position of the three-dimensional area based on the information received by the input unit 141.

Sixth Embodiment

The embodiments described above are modifiable as other embodiments. Therefore, in a sixth embodiment, variations of the embodiments will be explained.

Processing Entity

In the embodiments described above, the terminal apparatus 140 acquires a parallax image group from the image storage apparatus 120, generates a graphic image indicating the position of a cursor in the depth direction in the stereoscopic image space, and displays superimposed images in which the graphic image is superimposed over a parallax image group on the stereoscopic display monitor 142. However, the embodiments are not limited thereto. For example, the workstation 130 may be provided with the same functions as that of the terminal apparatus 140, 240, 340, 440, or 540, for example, and generate the graphic image. In such a case, the workstation 130 acquires the position information of the cursor from the terminal apparatus 140, and generates a graphic image based on the cursor position information thus acquired. The workstation 130 then generates superimposed images in which the graphic image is superimposed over a parallax image group generated from volume data, and stores the superimposed images thus generated in the image storage apparatus 120 or transmits the superimposed images thus generated to the terminal apparatus 140. The terminal apparatus 140 then receives superimposed images generated by the workstation 130 from the image storage apparatus 120 or the workstation 130, and displays the superimposed images thus received on the stereoscopic display monitor 142.

To specifically explain the process in which the workstation 130 generates a graphic image, for example, the workstation 130 includes a graphic image generator that generates the three-dimensional graphic data by plotting image data of a cursor and image data of a graphic indicating the cursor position in the cursor virtual space, in the same manner as the graphic image generator 1452 and the like. The image correction processor 1361a in the rendering processor 136 generates a single piece of volume data by fusing the three-dimensional graphic data generated by the graphic image generator and the volume data generated by the medical image diagnostic apparatus 110. The three-dimensional image processor 1362 in the rendering processor 136 then generates a parallax image group by applying a volume rendering process to the volume data fused by the image correction processor 1361a. The parallax image group, for example, corresponds to the nine superimposed images in which the parallax images U11 to U19 and the graphic images O11 to O19 are superimposed, as illustrated in the example in FIGS. 9A and 9B. Therefore, the terminal apparatus 140 can display various images illustrated as an example in FIG. 10 by displaying a parallax image group generated by the workstation 130, for example.

In the example explained above, the rendering processor 136 does not necessarily need to fuse the volume data and the three-dimensional graphic data. To explain more specifically, the workstation 130 includes a graphic image generator that generates three-dimensional graphic data by plotting image data of a cursor and image data of a graphic indicating the cursor position in the cursor virtual space, in the same manner as in the examples explained above. The three-dimensional image processor 1362 in the rendering processor 136 then generates a parallax image group by applying a volume rendering process to the volume data generated by the medical image diagnostic apparatus 110, and generates a graphic image by applying a volume rendering process to the three-dimensional graphic data generated by the graphic image generator. The two-dimensional image processor 1363 in the rendering processor 136 then superimposes the parallax image group and the graphic image generated by the three-dimensional image processor 1362, in the same manner as the graphic image generator 1452 and the like.

Furthermore, in the example explained above, instead of causing the workstation 130 to generate a parallax image group from the volume data, the medical image diagnostic apparatus 110 may include a function equivalent to the function of the rendering processor 136, and generate a parallax image group from the volume data. In such a case, the terminal apparatus 140 acquires a parallax image group from the medical image diagnostic apparatus 110, and displays superimposed images in which graphic images are superimposed over the parallax image group thus acquired on the stereoscopic display monitor 142.

Furthermore, the terminal apparatus 140 may include a function equivalent to the function of the rendering processor 136, acquire the volume data from the medical image diagnostic apparatus 110 or the image storage apparatus 120, and generate a parallax image group from the volume data thus acquired. In such a case, the terminal apparatus 140 displays superimposed images in which graphic images are superimposed over the parallax image group generated locally on the terminal apparatus 140 on the stereoscopic display monitor 142.

Number of Parallax Images

Explained in the embodiments is an example in which graphic images are superimposed over a parallax image group that includes mainly nine parallax images; however, an embodiment is not limited thereto. For example, the terminal apparatus 140 may superimpose graphic images over a parallax image group including two parallax images from the image storage apparatus 120, and display the superimposed images.

System Configuration

Among those processes explained in the embodiments, the whole or a part of the processes explained to be executed automatically may also be executed manually. Furthermore, the whole or a part of the processes explained to be performed manually may be performed automatically by known methods. In addition, processes, controlling processes, and specific names, and information including various types of data and parameters may be modified in any manner unless specified otherwise.

Furthermore, the elements included in each of the apparatuses illustrated in the drawings are provided to schematically depict their functionality, and are not necessarily configured physically in the manner illustrated in the drawings. In other words, specific configurations in which the apparatuses are distributed or integrated are not limited to those illustrated in the drawings, and the whole or a part of the apparatuses may be distributed or integrated functionally or physically in any units depending on various loads or utilization. For example, the controller 135 included in the workstation 130 may be provided as an external apparatus of the workstation 130, and is connected over a network.

Computer Program

The processes executed by the terminal apparatus 140, 240, 340, 440, or 540 in the embodiments may be described in a language executable by a computer as a computer program. In such a case, the same advantageous effects as those in the embodiments can be achieved by causing a computer to execute the computer program. Furthermore, the processes that are the same as those in the embodiments may also be realized by recording the computer program to a computer-readable recording medium, and causing a computer to read the computer program recorded in the recording medium. For example, such a computer program is stored in a hard disk, a flexible disk (FD), a compact disk read-only memory (CD-ROM), a magneto-optical (MO) disk, a digital versatile disk (DVD), a Blu-ray disk, or the like. Furthermore, such a computer program may also be distributed over a network such as the Internet.

According to at least one of the embodiments described above, an observer is enabled to recognize the position of the cursor, by generating a plurality of parallax images by applying a rendering process to volume data that is three-dimensional medical image data from a plurality of viewpoint positions, and displaying the parallax images and graphic images representing the depth-direction position of a cursor that is operable by a pointing device in a three-dimensional stereoscopic image space where a stereoscopic image is displayed by the stereoscopic display apparatus on a stereoscopic display apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system comprising:
a stereoscopic display apparatus configured to display a stereoscopic image enabled for a stereoscopic vision using a plurality of parallax images;
a rendering processor configured to generate a plurality of parallax images by applying a rendering process to volume data that is three-dimensional medical image data, from a plurality of viewpoint positions having different relative positions with respect to the volume data; and
a display controller configured to cause the stereoscopic display apparatus to display a graphic image that includes a cursor that is operable by a given input unit in a three-dimensional stereoscopic image space in which a stereoscopic image is displayed on the stereoscopic display apparatus and an image of a given graphic indicating a depth-direction position of the cursor in a three-dimensional space represented by a coordinate system of the volume data, together with the parallax images generated by the rendering processor, wherein the cursor is applied with a different color corresponding to the depth-direction position of the cursor and
the image of the given graphic indicates a distribution of colors that are applied to the cursor corresponding to the depth-direction position and having a shape extending in the depth direction.

2. The image processing system according to claim 1, further comprising:
a graphic image generator configured to generate a plurality of graphic images by generating three-dimensional graphic data by plotting image data of the cursor and the given graphic in a cursor virtual space that is a three-dimensional space represented by a same coordinate system as that of the volume data and in which position information of the cursor is managed, the given graphic indicating the depth-direction position of the cursor in the virtual space, and applying a rendering process to the three-dimensional graphic data thus generated from the viewpoint positions, wherein
the display controller is configured to cause the stereoscopic display apparatus to display superimposed images in which, over the parallax images generated by the rendering processor, the respective graphic images generated by the graphic image generator and having a matched viewpoint position are superimposed.

3. The image processing system according to claim 2, wherein
the graphic image generator is configured
to generate the three-dimensional graphic data based on a position of an image of a region in a subject represented by the volume data, by plotting image data of a line connecting the cursor and the image of the region, as the image data of the given graphic, on a plane at a same depth-direction position as the cursor in the cursor virtual space.

4. The image processing system according to claim 2, wherein the graphic image generator is configured to generate the three-dimensional graphic data based on a position of an image of a region in a subject represented by the volume data, by plotting image data of a plane including the position of the cursor and the position of the image of the region, as the image data of the given graphic, on a plane at a same depth-direction position as the cursor in the cursor virtual space.

5. The image processing system according to claim 4, wherein the graphic image generator is configured to generate the three-dimensional graphic data by plotting image data of a plane including the position of the cursor and the position of the image of the region, and image data of a perpendicular plane perpendicularly intersecting with the plane, as the image data of the given graphic, in the cursor virtual space.

6. The image processing system according to claim 2, wherein the graphic image generator is configured to generate the three-dimensional graphic data based on a position of an image of a region in a subject represented by the volume data, by plotting image data of a contour line indicating a depth-direction component to a position corresponding to a surface of the image of the region in the cursor virtual space.

7. The image processing system according to claim 2, wherein the graphic image generator is configured to generate the three-dimensional graphic data by plotting image data of the cursor that is applied with a different color corresponding to the depth-direction position of the cursor, as the image data of the given graphic, in the cursor virtual space.

8. The image processing system according to claim 7, wherein the graphic image generator is configured to generate the three-dimensional graphic data by plotting the image of the given graphic indicating a distribution of colors that are applied to the cursor corresponding to the depth-direction position, the image data having a shape extending in the depth direction, in the cursor virtual space.

9. The image processing system according to claim 2, further comprising:
a light source setting module configured to set a virtual light source that is a virtual light source to a given position in the cursor virtual space, wherein
the graphic image generator is configured, when an image of a region in a subject represented by the volume data is present between the virtual light source set by the light source setting module and the cursor, to generate the three-dimensional graphic data by plotting image data of the cursor on which a shadow of the image of the region is projected in the cursor virtual space.

10. The image processing system according to claim 9, wherein the graphic image generator is configured to change lightness of the shadow of the image of the region projected on the cursor depending on a distance between the cursor and the image of the region.

11. The image processing system according to claim 2, wherein the display controller is configured to display the stereoscopic image with lightness or contrast varied in radial directions, centering on the position of the cursor in response to a given operation.

12. The image processing system according to claim 11, wherein the display controller is configured to display the stereoscopic image so that lightness or contrast of a given area including the position of the cursor is varied in response to a given operation.

13. The image processing system according to claim 2, wherein the display controller is configured to display a given area including the position of the cursor and an area other than the given area in different colors, contrast, or lightness in response to a given operation.

14. The image processing system according to claim 1, further comprising:
a graphic image generator configured to generate three-dimensional graphic data by plotting image data of the cursor and the given graphic in a cursor virtual space that is a three-dimensional space represented by a same coordinate system as that of the volume data and in which position information of the cursor is managed, the given graphic indicating the depth-direction position of the cursor in the virtual space, wherein
the rendering processor is configured to generate the parallax images by applying a rendering process to volume data in which the three-dimensional graphic data generated by the graphic image generator is synthesized with the volume data, from the viewpoint positions.

15. The image processing system according to claim 1, further comprising:
an operation controller configured to enable the cursor to be moved between positions in the cursor virtual space in which the image data of the given graphic is plotted by the graphic image generator in response to a given operation performed while a stereoscopic image is displayed on the stereoscopic display apparatus.

16. An image processing apparatus comprising:
a stereoscopic display apparatus configured to display a stereoscopic image enabled for a stereoscopic vision using a plurality of parallax images;
a rendering processor configured to generate a plurality of parallax images by applying a rendering process to volume data that is three-dimensional medical image data from a plurality of viewpoint positions having different relative positions with respect to the volume data; and
a display controller configured to cause the stereoscopic display apparatus to display a graphic image that includes a cursor that is operable by a given input unit in a three-dimensional stereoscopic image space in which a stereoscopic image is displayed on the stereoscopic display apparatus and an image of a given graphic indicating a depth-direction position of the cursor in a three-dimensional space represented by a coordinate system of the volume data, together with the parallax images generated by the rendering processor, wherein
the cursor is applied with a different color corresponding to the depth-direction position of the cursor and
the image of the given graphic indicates a distribution of colors that are applied to the cursor corresponding to the depth-direction position and having a shape extending in the depth direction.

17. An image processing method executed by an image processing system including a stereoscopic display apparatus that displays a stereoscopic image enabled for a stereoscopic vision using a plurality of parallax images, the image processing method comprising:
generating a plurality of parallax images by applying a rendering process to volume data that is three-dimensional medical image data from a plurality of viewpoint positions having different relative positions with respect to the volume data; and
displaying a graphic image that includes a cursor that is operable by a given input unit in a three-dimensional stereoscopic image space in which a stereoscopic image is displayed on the stereoscopic display apparatus and an image of a given graphic indicating a depth-direction position of the cursor in a three-dimensional space represented by a coordinate system of the volume data, together with the parallax images generated, on the stereoscopic display apparatus, wherein
the cursor is applied with a different color corresponding to the depth-direction position of the cursor and
the image of the given graphic indicates a distribution of colors that are applied to the cursor corresponding to the depth-direction position and having a shape extending in the depth direction.

* * * * *